(12) United States Patent
Lisanti et al.

(10) Patent No.: US 11,229,657 B2
(45) Date of Patent: Jan. 25, 2022

(54) TARGETING HYPOXIC CANCER STEM CELLS (CSCS) WITH DOXYCYCLINE: IMPLICATIONS FOR IMPROVING ANTI-ANGIOGENIC THERAPY

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 88 days.

(21) Appl. No.: 16/606,849

(22) PCT Filed: Apr. 20, 2018

(86) PCT No.: PCT/US2018/028601
§ 371 (c)(1),
(2) Date: Oct. 21, 2019

(87) PCT Pub. No.: WO2018/195446
PCT Pub. Date: Oct. 25, 2018

(65) Prior Publication Data
US 2020/0046740 A1 Feb. 13, 2020

Related U.S. Application Data

(60) Provisional application No. 62/488,483, filed on Apr. 21, 2017.

(51) Int. Cl.
| | | |
|---|---|---|
| A61K 31/65 | (2006.01) | |
| A61P 35/00 | (2006.01) | |
| A61K 31/66 | (2006.01) | |
| A61K 31/337 | (2006.01) | |

(52) U.S. Cl.
CPC ............ *A61K 31/65* (2013.01); *A61K 31/337* (2013.01); *A61K 31/66* (2013.01); *A61P 35/00* (2018.01)

(58) Field of Classification Search
CPC ................................ A61P 35/00; A61K 31/65
See application file for complete search history.

(56) References Cited

U.S. PATENT DOCUMENTS

| | | |
|---|---|---|
| 3,517,067 A | 6/1970 | Stern |
| 5,168,057 A | 12/1992 | Oh et al. |
| 5,250,518 A | 10/1993 | Kobrehel et al. |
| 5,441,939 A | 8/1995 | Yang |
| 5,795,871 A | 8/1998 | Narita et al. |
| 5,837,696 A | 11/1998 | Golub et al. |
| 6,043,226 A | 3/2000 | Lundy et al. |
| 6,165,999 A | 12/2000 | Vu |
| 6,475,518 B1 | 11/2002 | Baumgart et al. |
| 6,858,598 B1 | 2/2005 | McKearn et al. |
| 7,405,227 B2 | 7/2008 | Kun et al. |
| 7,485,298 B2 | 2/2009 | Powell |
| 8,075,902 B2 | 12/2011 | Powell |
| 8,357,723 B2 | 1/2013 | Satyam |
| 8,741,853 B2 | 6/2014 | Steliou |
| 9,394,233 B2 | 7/2016 | Merino et al. |
| 9,622,982 B2 | 4/2017 | Bannister et al. |
| 9,675,578 B2 | 6/2017 | Desai et al. |
| 9,801,922 B2 | 10/2017 | Spitz et al. |
| 2001/0002404 A1 | 5/2001 | Webb |
| 2005/0002942 A1 | 1/2005 | Vlahov et al. |
| 2005/0209292 A1 | 9/2005 | Chuang et al. |
| 2005/0256081 A1 | 11/2005 | Peyman |
| 2007/0048296 A1 | 3/2007 | Kajander et al. |
| 2007/0105937 A1 | 5/2007 | Pappolla et al. |
| 2008/0045589 A1 | 2/2008 | Kelley |
| 2008/0160007 A1 | 7/2008 | Powell |
| 2008/0241959 A1 | 10/2008 | Culic et al. |
| 2009/0311249 A1 | 12/2009 | Gianni et al. |
| 2010/0120679 A1 | 5/2010 | Xu et al. |
| 2010/0202969 A1 | 8/2010 | Panyam et al. |
| 2010/0285001 A1 | 11/2010 | Land et al. |
| 2012/0141467 A1 | 6/2012 | Schneider |
| 2014/0142056 A1 | 5/2014 | Shanmugam et al. |
| 2014/0187611 A1 | 7/2014 | Auwerx et al. |
| 2014/0303085 A1 | 10/2014 | Wong et al. |
| 2014/0364595 A1 | 11/2014 | Bapat et al. |
| 2015/0079154 A1 | 3/2015 | Zender et al. |

(Continued)

FOREIGN PATENT DOCUMENTS

| | | |
|---|---|---|
| EP | 0656422 | 6/1995 |
| EP | 0941998 | 9/2004 |

(Continued)

OTHER PUBLICATIONS

Vredenburgh et al., "Bevacizumab plus irinotecan in recurrent glioblastoma multiforme," J. Clin. Oncol. 25(30), 4722-29. PMID: 17947719. (Year: 2007).*
Yang et al., "Doxycycline Induces Apoptosis and Inhibits Proliferation and Invasion of Human Cervical Carcinoma Stem Cells," PLoS One 10(6), e0129138. PMID: 26111245. (Year: 2015).*
Bizzarri et al., "Bevacizumab for the treatment of cervical cancer," Expert Opin. Biol. Ther. 16(3), 407-19. PMID: 26796332. (Year: 2016).*
Lamb, et al., "Antibiotics that target mitochondria effectively eradicate cancer stem cells, across multiple tumor types: Treating cancer like an infectious disease", Oncotarget, Jan. 22, 2015, vol. 6, No. 7, pp. 4569-4584.
Giacometti et al., "In-vitro activity of macrolides alone and in combination with artemisin, atovaquone, dapsone, minocycline or pyrimethamine against *Cryptosporidium parvum*", Journal of Antimicrobial Chemotherapy, 1996, vol. 38, pp. 399-408.

(Continued)

*Primary Examiner* — Theodore R. Howell
(74) *Attorney, Agent, or Firm* — Nixon & Vanderhye, P.C.

(57) ABSTRACT

The present disclosure relates to inhibitors of mitochondrial function. Methods of treating hypoxic cancer cells using anti-angiogenic agents and mitochondrial biogenesis inhibitors are disclosed. Tetracyclines, such as doxycycline, may serve as mitochondrial biogenesis inhibitors. Also described are methods of sensitizing hypoxic cancer cells to one or more chemotherapies by administering a mitochondrial biogenesis inhibitor with the chemotherapy.

16 Claims, 25 Drawing Sheets

(56) References Cited

U.S. PATENT DOCUMENTS

| | | |
|---|---|---|
| 2015/0224169 A1 | 8/2015 | Bhatia et al. |
| 2015/0224206 A1 | 8/2015 | Van |
| 2015/0231069 A1 | 8/2015 | Modi |
| 2016/0008332 A1 | 1/2016 | Haq et al. |
| 2016/0075726 A1 | 3/2016 | Neuzil |
| 2016/0339106 A1 | 11/2016 | Shanta |
| 2017/0014361 A1 | 1/2017 | Dhar |
| 2017/0035832 A1 | 2/2017 | Liu et al. |
| 2017/0095460 A1 | 4/2017 | Fathi et al. |
| 2017/0224730 A1 | 8/2017 | Berenson |
| 2017/0232008 A1 | 8/2017 | Zeicher |
| 2018/0214472 A1 | 8/2018 | Bapat et al. |

FOREIGN PATENT DOCUMENTS

| | | | |
|---|---|---|---|
| JP | 2016-155679 | 9/2016 | |
| WO | 1995015770 | 6/1995 | |
| WO | 99/26582 | 6/1999 | |
| WO | WO 2008/029085 A1 | 4/2008 | |
| WO | WO 2008/145116 | 12/2008 | |
| WO | WO-2009036108 A1 * | 3/2009 | ........... A61K 31/336 |
| WO | 2010/121177 | 10/2010 | |
| WO | WO 2011/031474 A2 | 3/2011 | |
| WO | 2013/040206 | 3/2013 | |
| WO | 2015/191668 | 12/2015 | |
| WO | 2016/027089 | 2/2016 | |
| WO | 2016/059247 | 4/2016 | |
| WO | 2018/027252 | 2/2018 | |
| WO | 2018/136598 | 7/2018 | |
| WO | 2018/136617 | 7/2018 | |
| WO | 2018/195434 | 10/2018 | |
| WO | 2018/195446 | 10/2018 | |
| WO | 2018/202910 | 11/2018 | |
| WO | 2018/213751 | 11/2018 | |
| WO | 2018/213764 | 11/2018 | |
| WO | 2018/218242 | 11/2018 | |
| WO | WO 2019104115 | 5/2019 | |
| WO | WO 2019126179 | 6/2019 | |

OTHER PUBLICATIONS

M2 Pharma [London], "Study finds vitamin C and antibiotics effectively killed cancer stem cells", Jun. 13, 2017, 2 pages.
Sotgia et al., "A mitochondrial based oncology platform for targeting cancer stem cells (CSCs): MITO-ONC-RX", Journal Cell Cycle, Sep. 26, 2018, vol. 17, No. 17, pp. 2091-2100.
Komatsu et al., "Clarithromycin enhances bortezomib-induced cytotoxicity via endoplasmic reticulum stress-mediated CHOP (GADD153) induction and autophagy in breast cancer cells", International Journal of Oncology, vol. 40, 2012, pp. 1029-1039.
Moriya et al., "Macrolide antibiotics block autophagy flux and sensitize to bortezomib via endoplasmic reticulum stress-mediated CHOP induction in myeloma cells", International Journal of Oncology, vol. 42, 2013, pp. 1541-1550.
Petovari et al., "Targeting cellular metabolism using rapamycin and/or doxycycline enhances anti-tumour effects in human glioma cells", Cancer Cell Int., 18:211, 2018, pp. 1-17.
Van Nuffel et al., "Repurposing Drugs in Oncology (ReDO)—clarithromycin as an anti-cancer agent", ecancermedicalscience, 2015, pp. 1-26.
Jankowitsch et al., "A novel N,N-8-amino-8-demethyl-D-riboflavin dimethyltransferase (RosA) catalyzing the two terminal steps of roseoflavin biosynthesis in *Streptomyces davawensis*", The American Society for Biochemistry and Molecular Biology, Inc., 2011, pp. 1-25.
Murphy, "Targeting lipophilic cations to mitochondria", Biochimica et Biophysica Acta, 2008, pp. 1028-1031.
Ross et al., "Lipophilic Triphenylphosphonium Cations as Tools in Mitochondrial Bioenergetics and Free Radical Biology", Biochemistry (Moscow), vol. 70, No. 2, 2005, pp. 222-230. [Translated from Biokhimiya].
Gonzalez et al., "Mitochondria, Energy and Cancer: The Relationship with Ascorbic Acid", JOM, vol. 25, No. 1, 2010, pp. 29-38.
U.S. Appl. No. 10/188,668, filed Jan. 29, 2019, Bannister et al.
Ritter et al., "The Combination of Antiangiogenic and Cytotoxic Agents in the Treatment of Prostate Cancer", Clin. Prostate Cancer 2(3): 153-59 (2003), PMID: 15040858.
Su et al., "Doxycycline Enhances the Inhibitory Effects of Bevacizumab on Corneal Neovascularization and Prevents Its Side Effects" Invest. Ophthalmol. Vis Sci. 52(12): 9108-15 (2011), PMID: 22039247.
Huie et al., "Phase II Study of Interferon-Alpha and Doxycycline for Advanced Renal Cell Carcinoma," Invest. New Drugs 24(3): 255-60 (2006). PMID: 16205854.
International Search Report and Written Opinion of the ISA for PCT/US2018/028601, dated Jul. 16, 2018, 8 pages.
Ernestina Marianna De Francesco et al., "Targeting hypoxic cancer stem cells (CSCs) with Doxycycline: Implications for optimizing anti-angiogenic therapy", ONCOTARGET, vol. 8, No. 34, Jun. 12, 2017, p. 56126-56142.
Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.

* cited by examiner

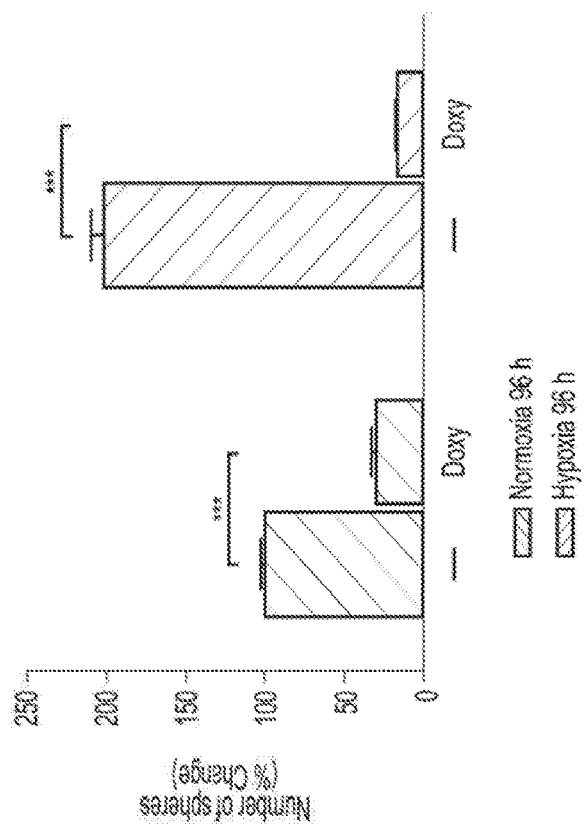
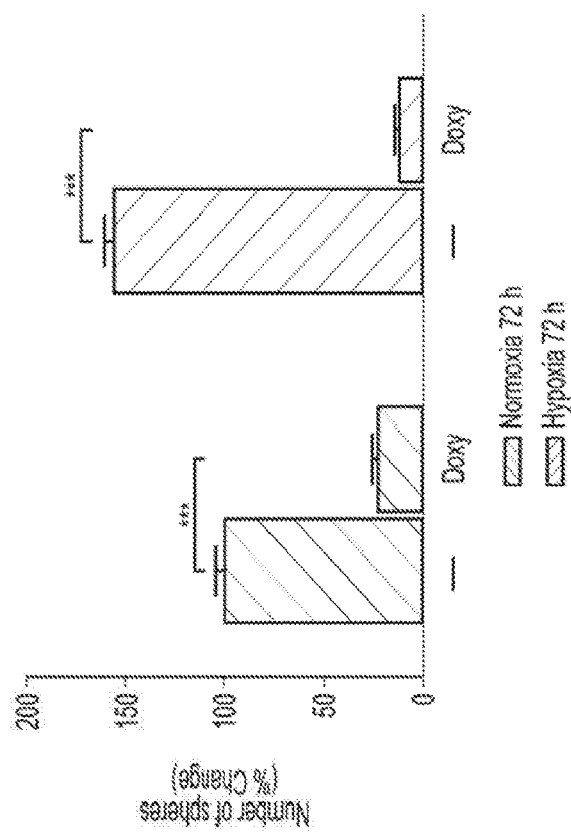
FIG. 4A
FIG. 4B

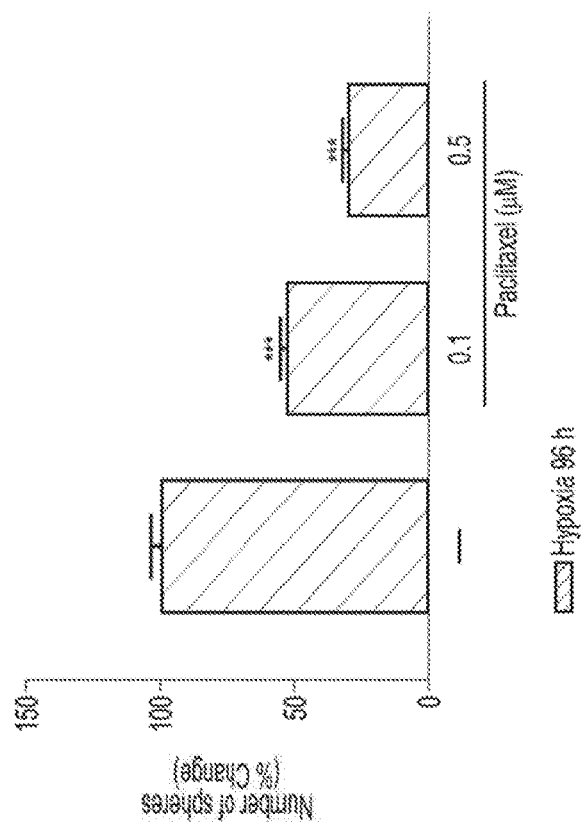
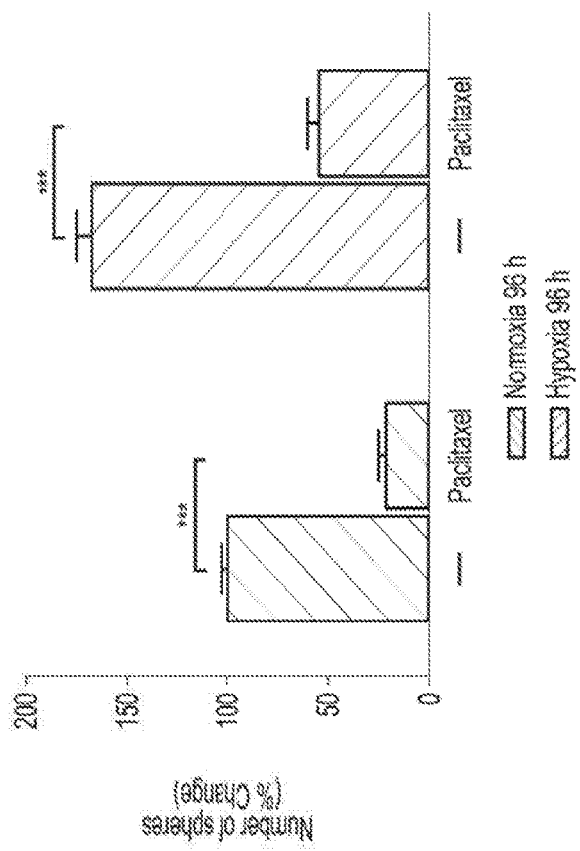
FIG. 5A
FIG. 5B

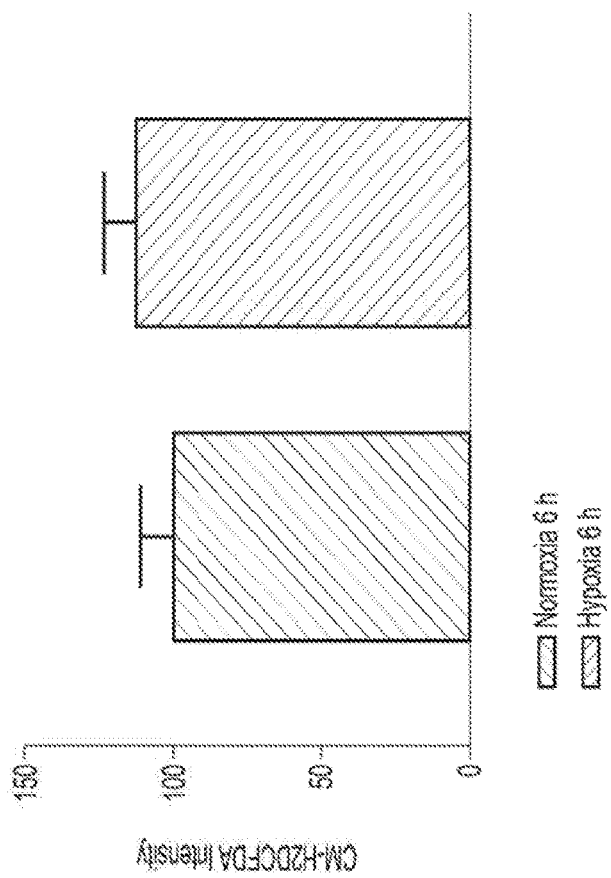
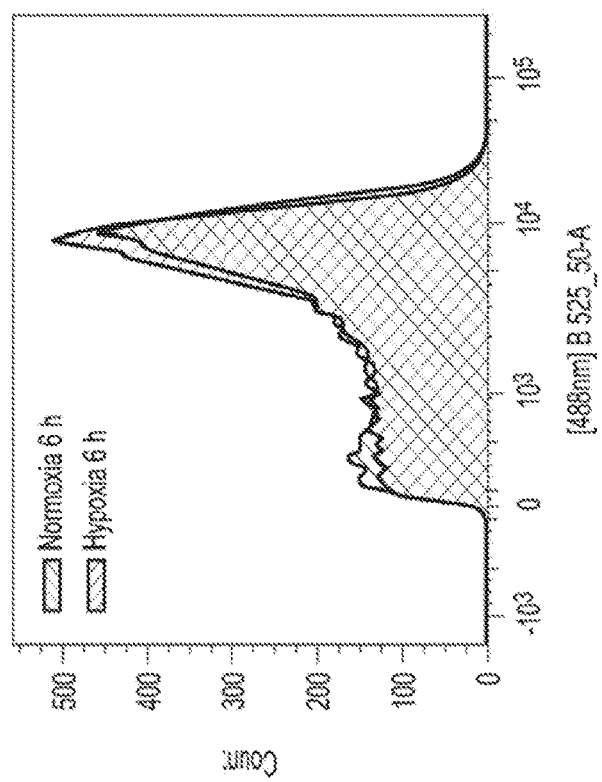
FIG. 9A
FIG. 9B

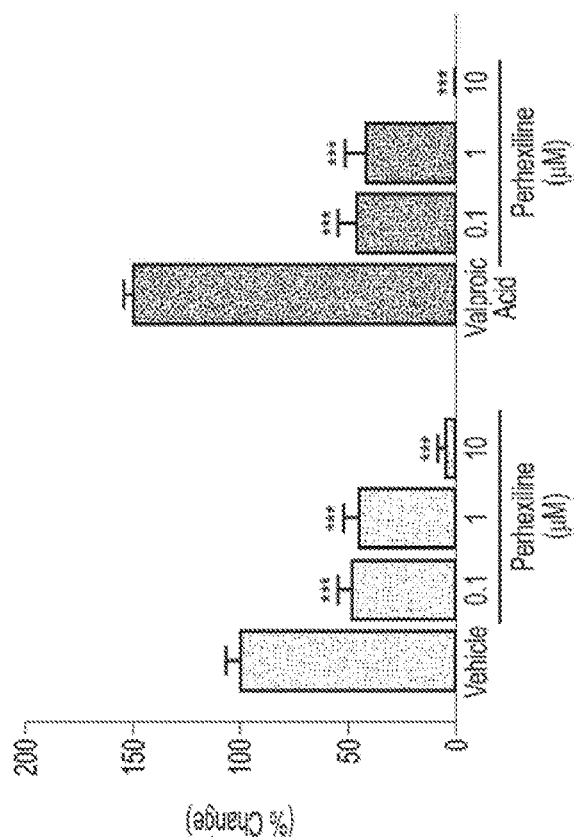
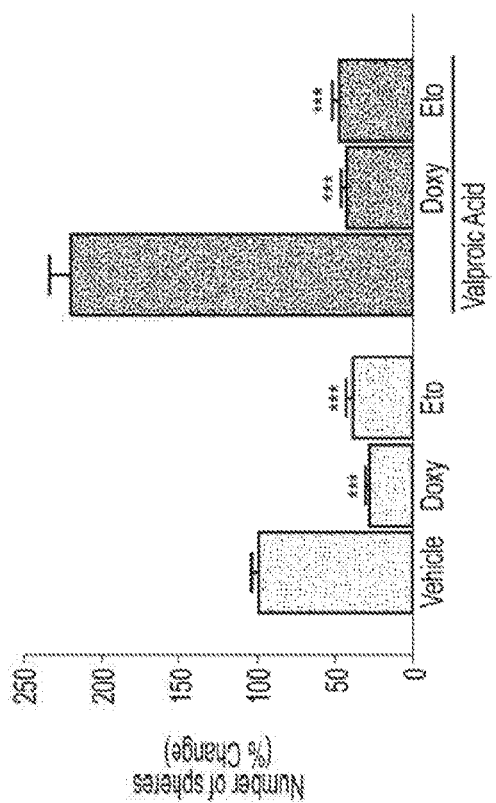
FIG. 12A
FIG. 12B

TARGETING HYPOXIC CANCER STEM CELLS (CSCS) WITH DOXYCYCLINE: IMPLICATIONS FOR IMPROVING ANTI-ANGIOGENIC THERAPY

CROSS-REFERENCE TO RELATED APPLICATIONS

This application is the U.S. national phase of International Application No. PCT/US2018/028601 filed 20 Apr. 2018, which designated the U.S. and claims the benefit of U.S. Provisional Patent Application No. 62/488,483, filed Apr. 21, 2017, the entire contents of each of which are hereby incorporated herein by reference.

FIELD

The present disclosure relates to methods of eradicating hypoxic cancer stem cells using inhibitors of mitochondrial biogenesis with anti-angiogenic therapies, and to methods of sensitizing hypoxic cancer cells to chemotherapies by treating the cells with one or more mitochondrial biogenesis inhibitors.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Hypoxia in the tumor microenvironment is a negative prognostic factor that ultimately promotes cancer progression, tumor recurrence, distant metastasis, and chemo- and radio-resistance. Hypoxia can induce stem cell characteristics in cancer cells. Increases in "sternness" may explain the clinical association of hypoxia with poor prognosis and drug-resistance. There remains a need to develop "hypoxia-specific" therapeutics to target hypoxic microenvironments.

SUMMARY

The present disclosure relates to methods of treating hypoxic cancer stem cells (CSCs) by administering a therapeutically effective amount of an anti-angiogenic agent and a therapeutically effective amount of a mitochondrial biogenesis inhibitor to a patient in need thereof. In some embodiments, the anti-angiogenic agent includes at least one of bevacizumab, itraconazole, carboxyamidotriazole, TNP-470, CM101, INF-alpha, IL-12, platelet factor-4, suramin, SU5416, thrombospondin, a VEGFR antagonist, an angiostatic steroid plus heparin, Cartilage-Derived Angiogenesis Inhibitory Factor, a matrix metalloproteinase inhibitor, angiostatin, endostatin, 2-methoxyestradiol, tecogalan, tetrathiomolybdate, thalidomide, thrombospondin, prolactin, linomide, αVβ3 inhibitors, ramucirumab, tasquinimod, ranibizumab, sorafenib, sunitinib, pazopanib, and everolimus. In some embodiments, the mitochondrial biogenesis inhibitor includes at least one of a tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin.

The present disclosure also relates to methods of sensitizing hypoxic CSCs to one or more chemotherapies, the method including: administering a therapeutically effective amount of a mitochondrial biogenesis inhibitor with the chemotherapy to a patient in need thereof. In some embodiments, the mitochondrial biogenesis inhibitor may include at least one of a tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin. In some embodiments, the chemotherapy is paclitaxel.

The present disclosure also relates to methods of sensitizing hypoxic CSCs to radiotherapy. A therapeutically effective amount of a mitochondrial biogenesis inhibitor with radiotherapy may be administered to a patient in need thereof. In some embodiments, the mitochondrial biogenesis inhibitor may include at least one of a tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin.

BRIEF DESCRIPTION OF THE DRAWINGS

FIGS. 4A-B show that doxycycline treatment inhibits hypoxia-induced mammosphere formation in MCF7 cells.

FIGS. 5A-C show that a fraction of CSCs is resistant to Paclitaxel treatment (resistance measured by mammosphere formation), but that doxycycline treatment inhibits Paclitaxel-resistant CSC activity in MCF7 cells.

FIGS. 9A-D show the effects of chronic hypoxia on reactive oxygen species (ROS) production.

FIGS. 12A-C show that treatment with Etomoxir, Perhexiline, or glycolysis inhibitors inhibits basal and valproic acid-augmented CSC propagation, as measured by mammosphere formation.

DESCRIPTION

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondrial ribosome is an untapped gateway for treating a number of afflictions, ranging from cancer to bacterial and fungal infections to aging. Functional mitochondria are required for the propagation of CSCs. Inhibiting mitochondrial biogenesis in CSCs impedes the propagation of those cells. Mitochondrial inhibitors therefore represent a new class of anti-cancer therapeutics. The inventors hypothesized that mitochondrial inhibitors could be further used to target hypoxic CSCs.

Figure 1:
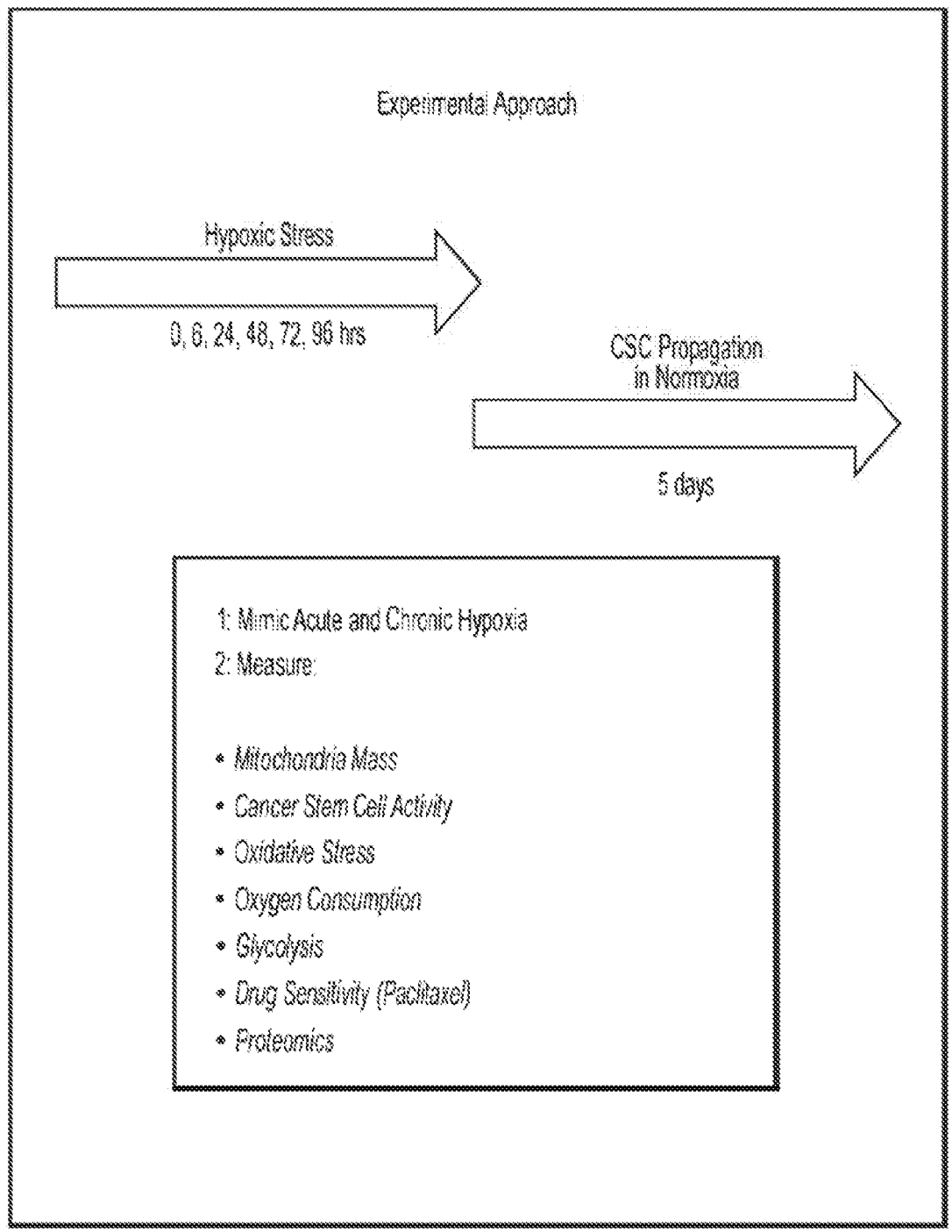
FIG. 1 outlines an experimental approach to study the role of chronic hypoxia and oxidative stress in the propagation of breast cancer stem cells (CSCs).
Figures 2A, 2B:
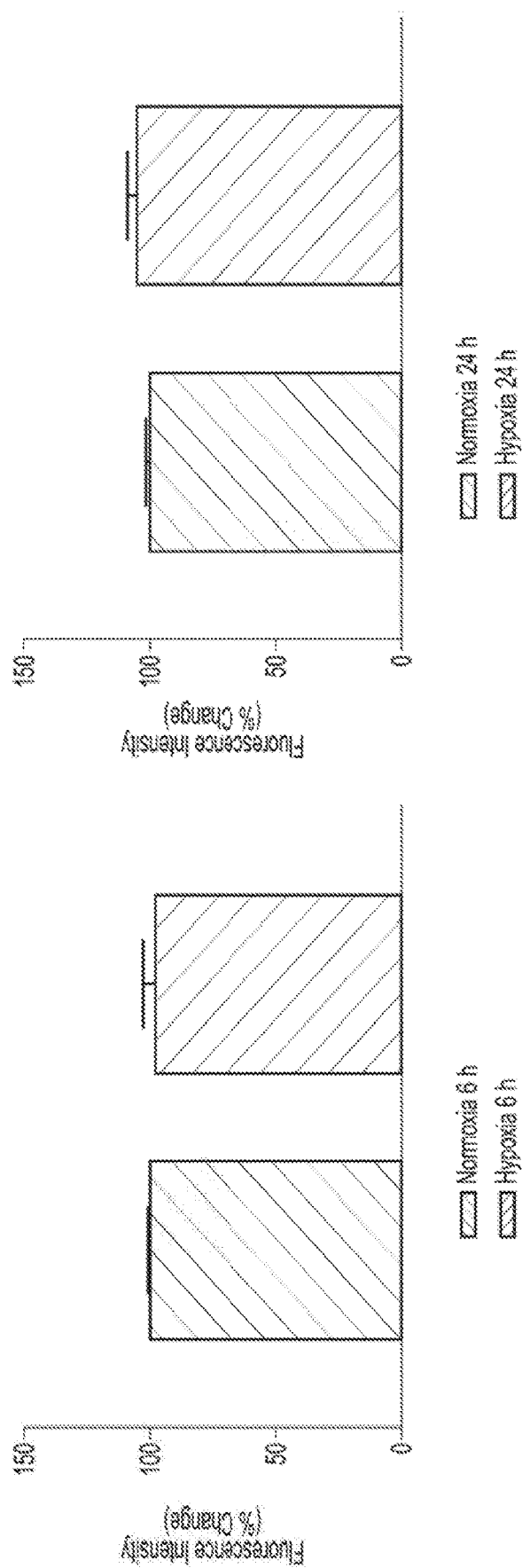
FIGS. 2A-F show the effects of chronic hypoxia on mitochondrial mass of MCF7 cells over time.
Figure 2D:
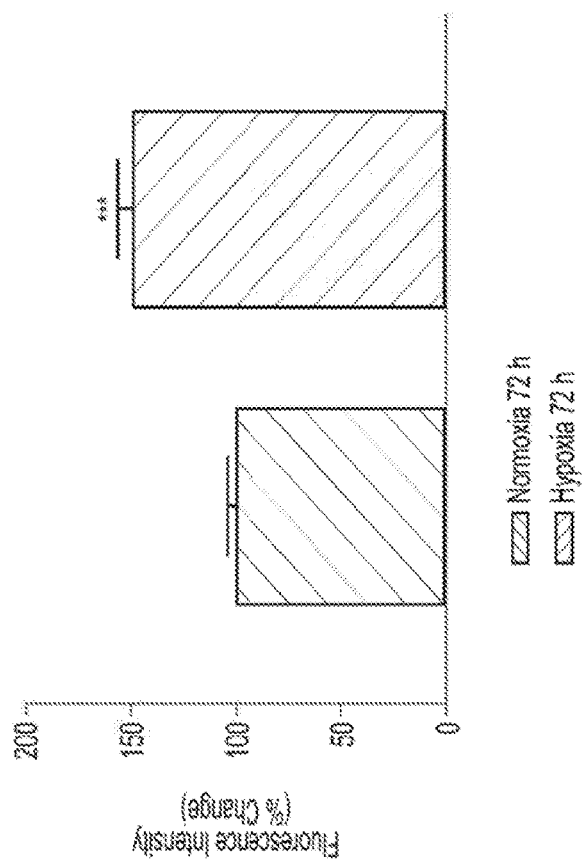
Figure 2C:
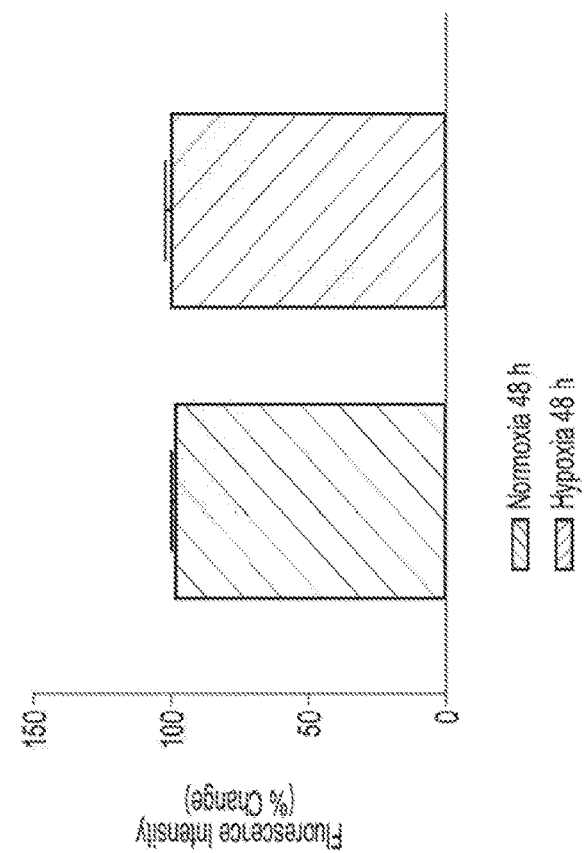
Figure 2E:
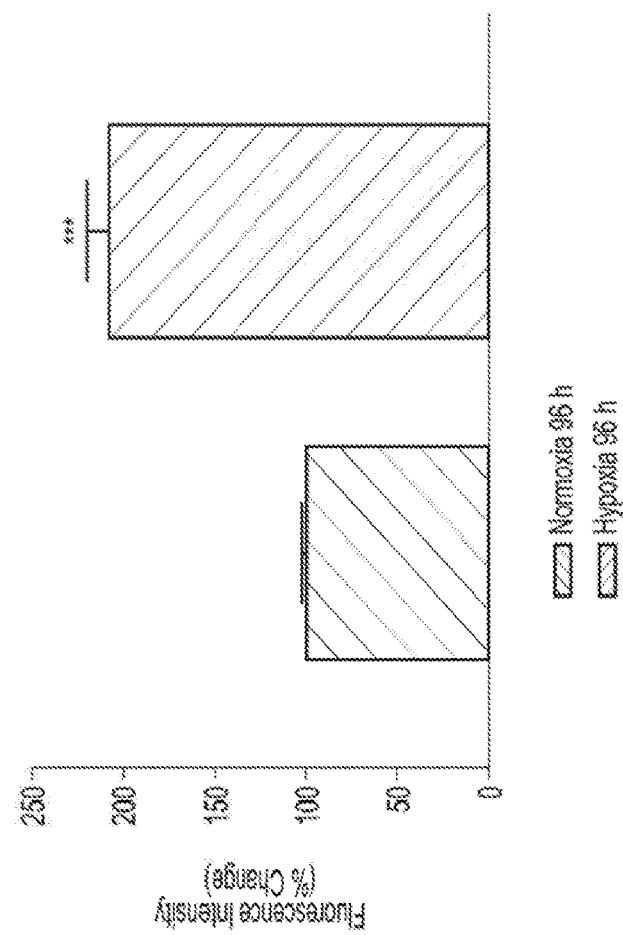
Figure 2F:
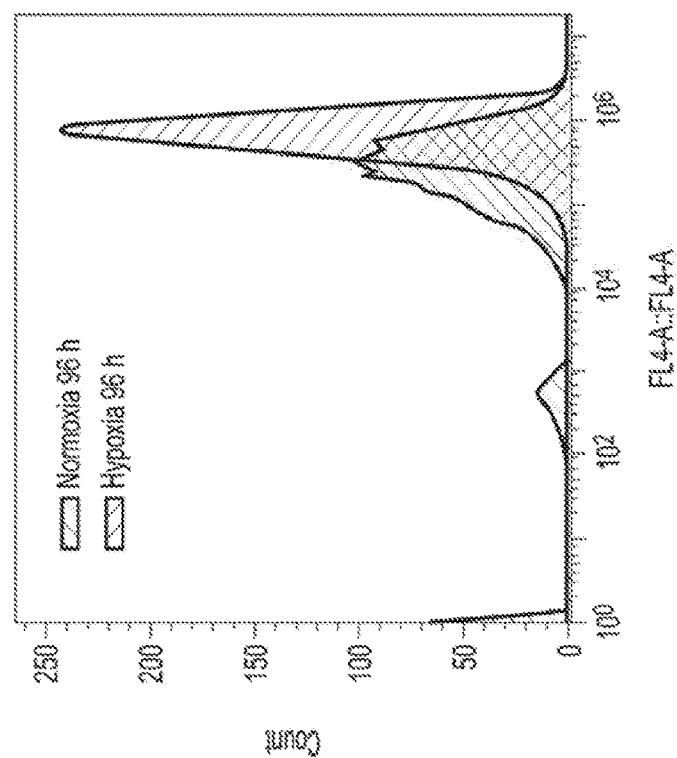
Figure 2H:
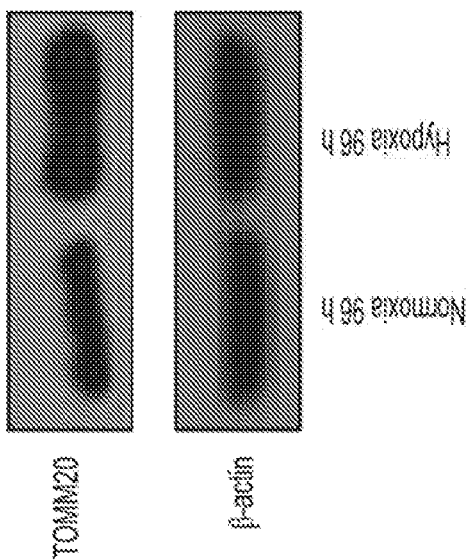
FIGS. 2G-H show the effects of chronic hypoxia on mitochondrial protein TOMM20 in MCF7 cells over time.
Figure 2G:
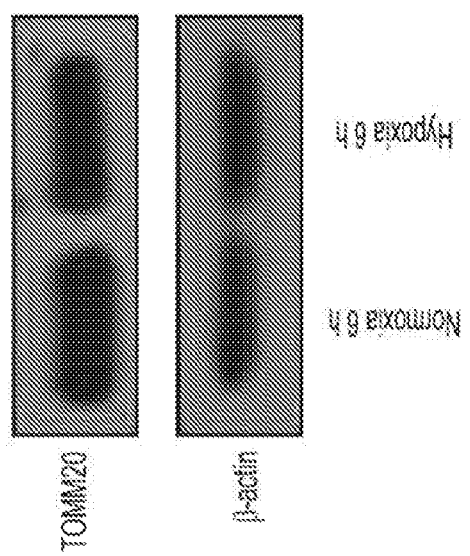

The inventors examined the effects of chronic hypoxia and oxidative stress on the propagation of breast CSCs using MCF7 cells as a model system. It should be appreciated that other model systems may be used. An outline of the experimental approach is shown in FIG. 1. Briefly, MCF7 cells were obtained from ATCC and cultured in DMEM (Sigma Aldrich). For hypoxic testing, MCF7 cells were cultured in low glucose DMEM in a multi-gas $N_2/CO_2$ hypoxic chamber at 1% O2. In parallel, MCF7 cells were cultured in low glucose DMEM at 21% O2 to serve as a normoxic control. MCF7 cell monolayers were subjected to hypoxia (1% oxygen) for increasing periods of time (0, 6, 24, 48, 72, and 96 hours). Next, the MCF7 cells were trypsinized and subjected to fluorescence-activated cell sorting (FACS) with MitoTracker Deep-Red-FM (Life Technologies). MitoTracker Deep Red localizes to mitochondria regardless of mitochondrial membrane potential. Cells were incubated with pre-warmed MitoTracker staining solution (diluted in PBS/CM to a final concentration of 10 nM) for 30-60 min at 37° C. All subsequent steps were performed in the dark. Cells were washed in PBS, harvested, re-suspended in 300 µL of PBS and then analyzed by flow cytometry (Fortessa, BD Bioscience). Data analysis was performed using FlowJo software (Tree star Inc.). FIGS. 2A-C show that 6, 24, and 48 hours of hypoxia had no significant effect on mitochondrial mass. In contrast, FIGS. 2D-E show that 72 and 96 hours of hypoxia treatment significantly increased mitochondrial mass. FIG. 2F is a representative FACS tracing showing 96 hours of hypoxia increased mitochondrial mass. The effects of hypoxia treatment were confirmed using immunoblot analysis with TOMM20, a marker of mitochondrial mass. FIG. 2G shows that 6 hours of hypoxia treatment has no effect on TOMM20 expression, whereas FIG. 2H shows that 96 hours of hypoxia treatment increases TOMM20 expression.

Figure 3B:
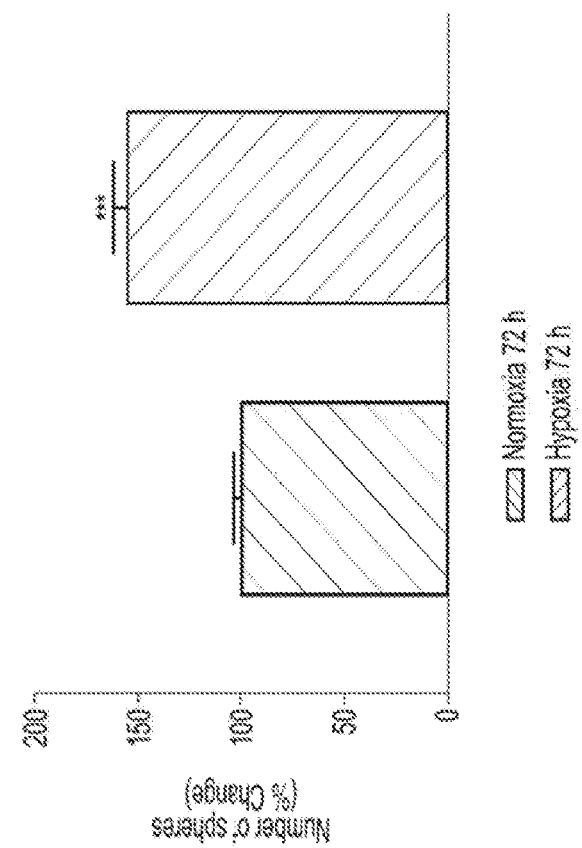
FIGS. 3A-C show the effects of chronic hypoxia on mammosphere formation in MCF7 cells.
Figure 3A:
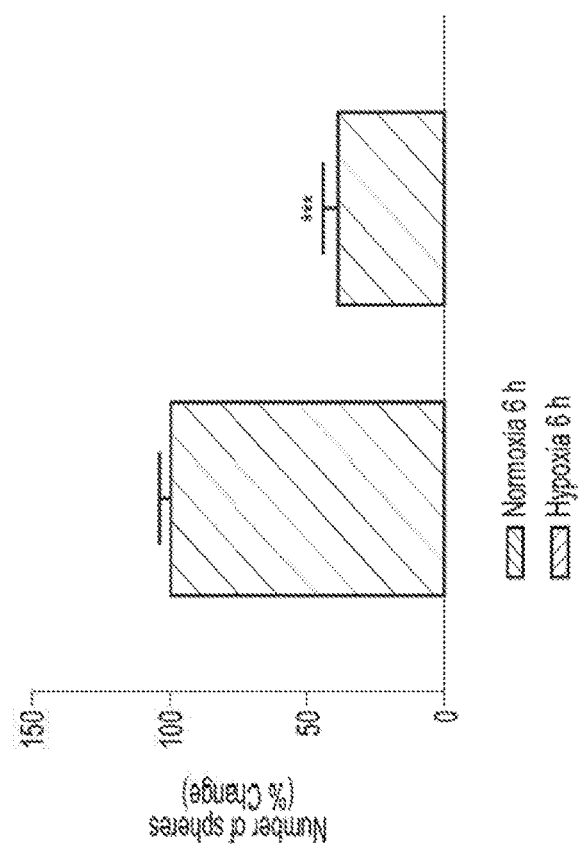
Figure 3C:
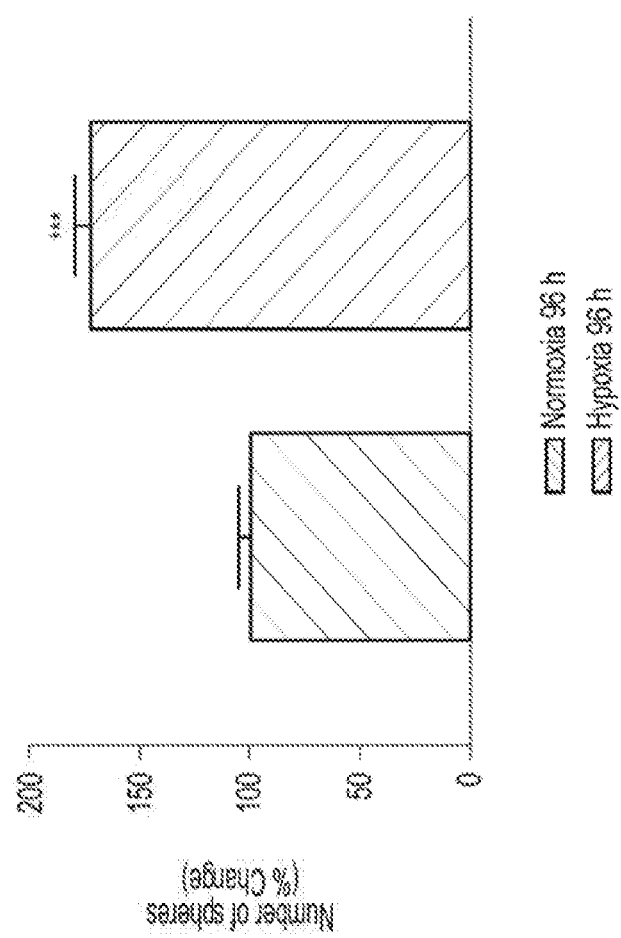

The effects of chronic hypoxia on CSC activity may be examined using mammosphere formation assays, though it should be appreciated by those of skill in the art that other assays may be used. Briefly, a single cell suspension of MCF7 cells previously exposed to normoxia (21% $O_2$) or hypoxia (1% $O_2$) for 6 h, 72 h or 96 h was prepared using enzymatic (1x Trypsin-EDTA, Sigma Aldrich) and manual disaggregation (25-gauge needle). Cells were plated at a density of 500 cells/cm$^2$ in mammosphere medium (DMEM-F12/B27/20-ng/ml EGF/PenStrep) in nonadherent conditions, in culture dishes coated with (2-hydroxyethylmethacrylate) (poly-HEMA, Sigma), in the presence of treatments. Cells were grown for 5 days and maintained in a humidified incubator at 37° C. at an atmospheric pressure in 5% (v/v) carbon dioxide/air. After five days of culturing, spheres greater than 50 µm in diameter were counted using an eye piece graticule, and the percentage of cells plated which formed spheres was calculated. Mammosphere assays were performed in triplicate and repeated three times independently. FIG. 3A shows that acute hypoxia (6 hour treatment) inhibited mammosphere formation by more than 60%. FIGS. 3B-C show that chronic hypoxia (72 and 96 hour treatments) increased mammosphere formation.

To determine whether mitochondrial biogenesis is required for hypoxia-induced CSC propagation, the inventors studied the effects of a mitochondrial biogenesis inhibitor. The antibiotic doxycycline is known to inhibit mitochondrial biogenesis, but it should be appreciated by those having skill in the art that other mitochondrial biogenesis inhibitors may be used. The inventors tested the effects of doxycycline on hypoxia-induced mammosphere formation. FIGS. 4A-B show that doxycycline treatment inhibited hypoxia-induced mammosphere formation under normoxic and hypoxic conditions.

Figure 5C:
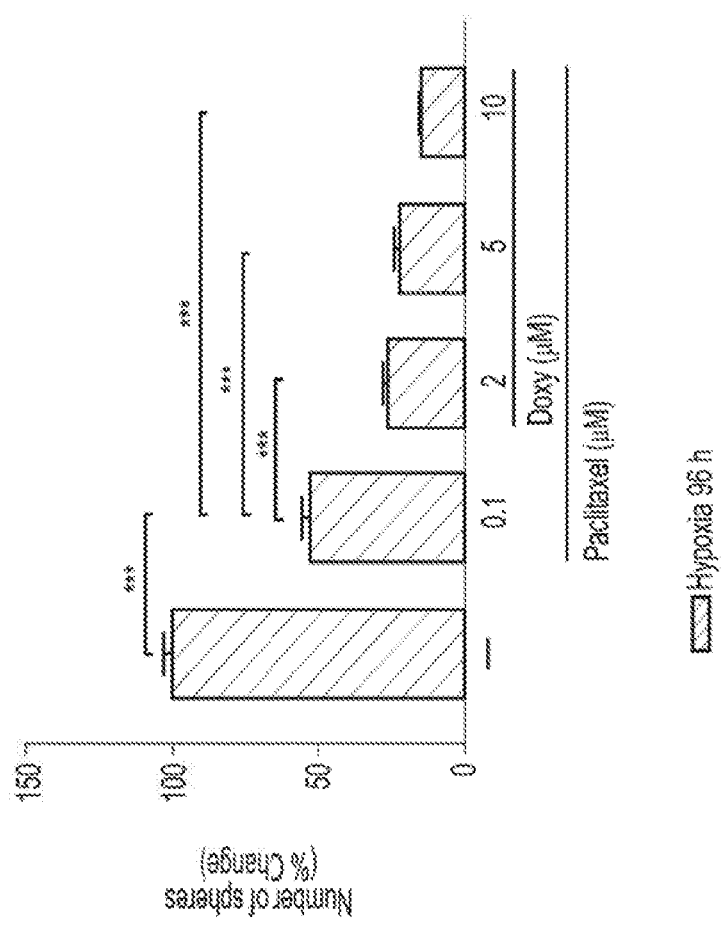

Hypoxic CSCs are known to be highly resistant to conventional chemotherapies such as Paclitaxel. The inventors hypothesized that mitochondrial biogenesis inhibitors may be used to sensitize hypoxic CSCSs to conventional chemotherapies. FIGS. 5A-B show that a fraction of CSCs is resistant to Paclitaxel treatment, but that doxycycline treatment significantly inhibits Paclitaxel-resistant CSC activity (FIG. 5C). Thus, mitochondrial biogenesis inhibitors may be used as adjuvants to decrease CSC resistance to chemotherapies.

Anti-angiogenic therapies have also emerged as promising anti-cancer agents, based on their ability to target tumor blood vessels and deprive the cells of essential nutrients. However, clinical and pre-clinical data have shown that long-term administration of anti-angiogenic agents can increase tumor invasiveness and metastasis. Failure of angiogenesis inhibitors may be due to their ability to generate intra-tumoral hypoxia, which stimulates CSCs survival and propagation. The combined use of doxycycline with angiogenesis inhibitors, such as bevacizumab (Avastin), itraconazole, carboxyamidotriazole, TNP-470 (analog of fumagillin), CM101, INF-alpha, IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, angiostatin, endostatin, 2-methoxyestradiol, tecogalan, tetrathiomolybdate, thalidomide, thrombospondin, prolactin, linomide, αvβ3 inhibitors, ramucirumab, tasquinimod, ranibizumab, sorafenib (Nexavar®), sunitinib (Sutent®), pazopanib (Votrient®), and everolimus (Afinitor®) may effectively block both blood vessel formation and CSC propagation and make anti-angiogenic therapy more effective.

Figure 6B:
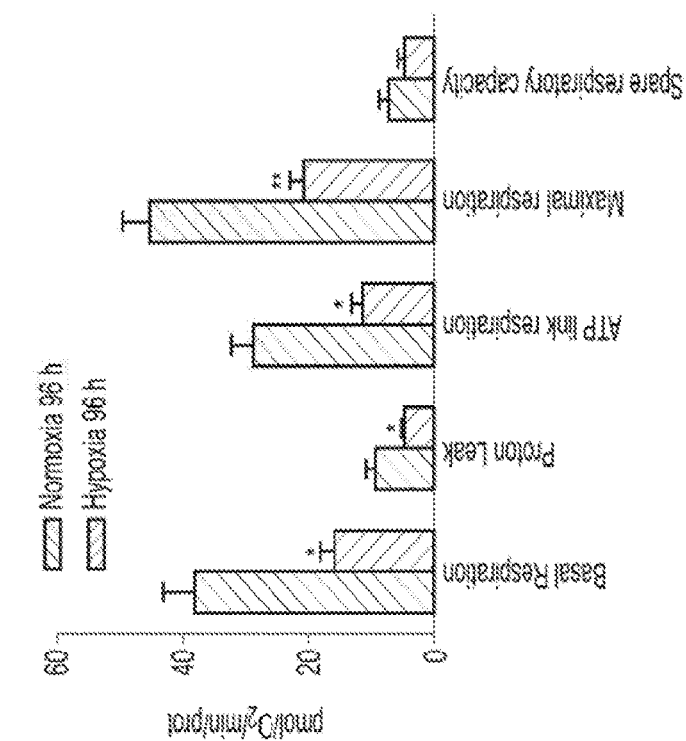
FIGS. 6A-B show the effects of hypoxia on oxygen consumption rates (OCR) over time in MCF7 cells.
Figure 6A:
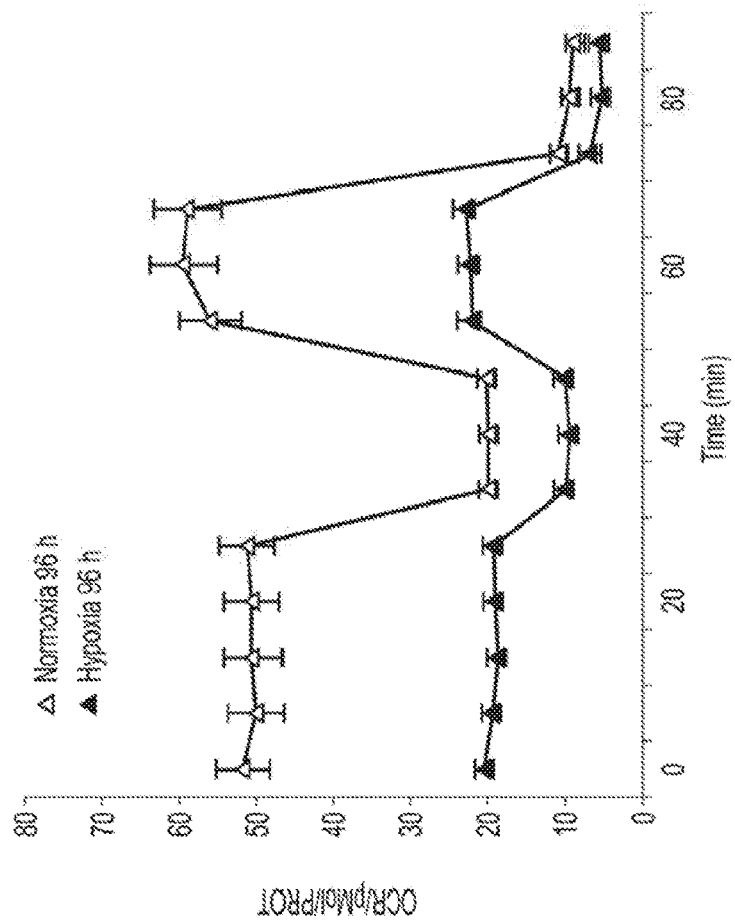
Figure 7B:
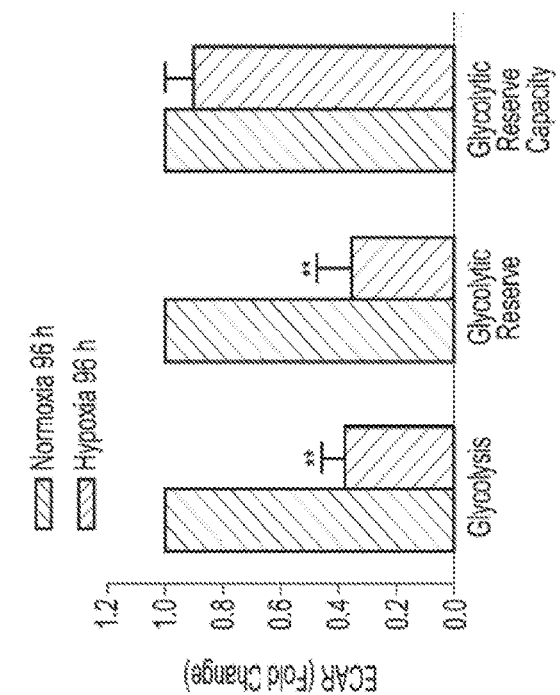
FIGS. 7A-B show the effects of hypoxia on extracellular acidification rates (ECAR) over time in MCF7 cells.
Figure 7A:
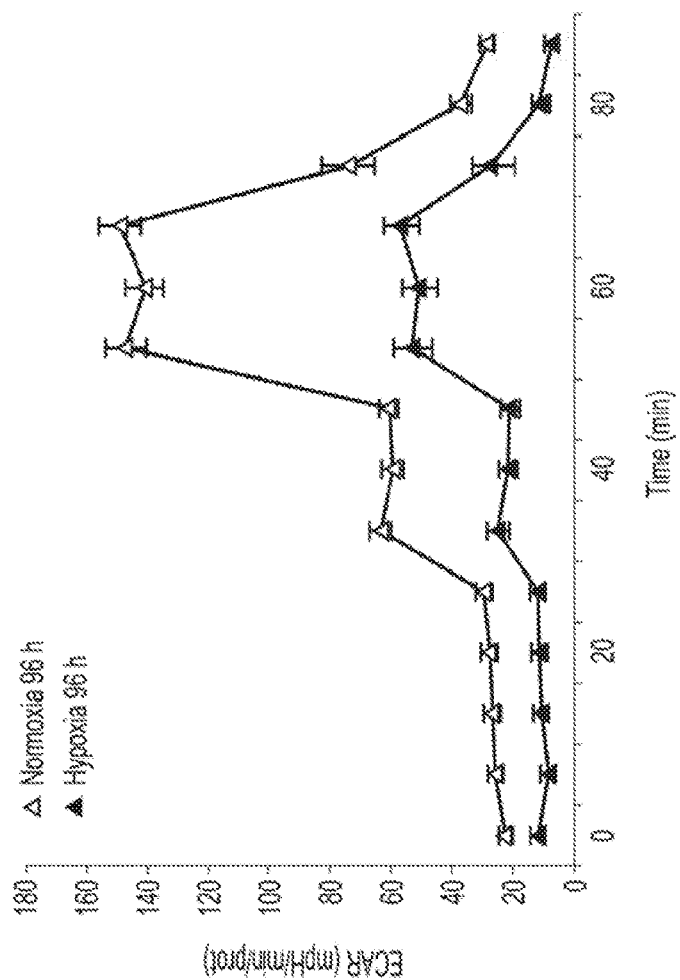

The present approach relates to methods of analyzing the effects of mitochondrial biogenesis inhibitors on the metabolic state of CSCs following chronic hypoxia treatment. For example, extracellular acidification rates (ECAR) and real-time oxygen consumption rates (OCR) for MCF7 cells may be determined using the Seahorse Extracellular Flux (XFe-96) analyzer (Seahorse Bioscience). After exposure to normoxia (21% $O_2$) or hypoxia (1% $O_2$) for 96 hours, 15,000 MCF7 cells per well were seeded into XFe-96 well cell culture plates for 24 hours. Then, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 µL/well of XF assay media at 37° C., in a non-$CO_2$ incubator for 1 hour. During the incubation time, 5 µL of 80 mM glucose, 9 µM oligomycin, and 1 M 2-deoxyglucose (for ECAR measurement) or 10 µM oligomycin, 9 µM FCCP, 10 µM Rotenone, 10 µM antimycin A (for OCR measurement), were loaded in XF assay media into the injection ports in the XFe-96 sensor cartridge. The data set was analyzed by XFe-96 software after the measurements were normalized by protein content (SRB). All experiments were performed three times independently FIGS. 6A-B show that chronic hypoxia decreased OCR. Similarly, glycolysis rates, as measured by ECAR, were reduced by more than 60% (FIG. 7A-B).

To further validate the functional observations from metabolic flux analysis, unbiased label-free proteomics analysis may be conducted to determine the effects of mitochondrial biogenesis inhibitors on the metabolic state of CSCs following chronic hypoxia treatment. Cell lysates were prepared for trypsin digestion by sequential reduction of disulphide bonds with TCEP and alkylation with MMTS. Then, the peptides were extracted and prepared for LC-MS/MS. All LC-MS/MS analyses were performed on an LTQ Orbitrap XL mass spectrometer (Thermo Scientific, San Jose, Calif.) coupled to an Ultimate 3000 RSLC nano system (Thermo Scientific, formerly Dionex, The Netherlands). Xcalibur raw data files acquired on the LTQ-Orbitrap XL were directly imported into Progenesis LCMS software (Waters Corp., Milford, Mass., formerly Non-linear dynamics, Newcastle upon Tyne, UK) for peak detection and alignment. Data were analyzed using the Mascot search engine. Five technical replicates were analyzed for each sample type. Table 1 shows three mitochondrial ribosomal proteins (MRPL4, MRPS35 and MRPL47) were upregulated in response to chronic hypoxia. Eleven other proteins related to mitochondrial biogenesis were upregulated, including: HYOU1, YARS2, NDUFV2, LONP1, POLRMT, COQ9, SARS2, HSPA9, HSPD1, ATP5J, and ATPAF1. Also, LRPPRC, a mitophagy inhibitor that prevents the autophagic digestion of mitochondria, was up-regulated. HYOU1 (hypoxia up-regulated protein 1), a mitochondrial chaperone protein that belongs to the heat shock protein 70 family and that is involved in mitochondrial protein folding and confers cyto-protection under hypoxic conditions, was overexpressed by more than 170-fold. Table 1 also shows other up-regulated proteins that are part of the OXPHOS complexes, such as NDUFV2.

TABLE 1

Mitochondrial Proteins Upregulated During Chronic Hypoxia (96 hours) in MCF7 Cells.

| Symbol | Description | Fold-Change (Up-regulation) |
| --- | --- | --- |
| HYOU1 | Hypoxia up-regulated protein 1 | 173.99 |
| DIABLO | Diablo homolog, mitochondrial | 51.91 |
| ECSIT | Evolutionarily conserved signaling intermediate in Toll pathway, mitochondrial | 32.26 |
| MRPL4 | 39S ribosomal protein L4, mitochondrial | 10.62 |
| PDK1 | [Pyruvate dehydrogenase (acetyl-transferring)] kinase isozyme 1, mitochondrial | 8.39 |
| HIBADH | 3-hydroxyisobutyrate dehydrogenase, mitochondrial | 8.28 |
| YARS2 | Tyrosine--tRNA ligase, mitochondrial | 7.58 |
| AK4 | Adenylate kinase 4, mitochondrial | 7.07 |
| NDUFV2 | NADH dehydrogenase [ubiquinone] flavoprotein 2, mitochondrial | 6.94 |
| ALDH6A1 | Methylmalonate-semialdehyde dehydrogenase [acylating], mitochondrial | 6.17 |
| MICU1 | Calcium uptake protein 1, mitochondrial | 5.1 |
| LONP1 | Lon protease homolog, mitochondrial | 4.36 |
| ACADSB | Short/branched chain specific acyl-CoA dehydrogenase, mitochondrial | 4.25 |
| MAVS | Mitochondrial antiviral-signaling protein | 4.12 |
| SLC25A1 | Mitochondrial 2-oxoglutarate/malate carrier protein | 3.39 |
| LRPPRC | Leucine-rich PPR motif-containing protein, mitochondrial | 2.92 |
| MTHFD2 | Bifunctional methylenetetrahydrofolate dehydrogenase/cyclohydrolase, mitochondrial | 2.63 |
| MRPS35 | 28S ribosomal protein S35, mitochondrial | 2.58 |
| ACAD9 | Acyl-CoA dehydrogenase family member 9, mitochondrial | 2.33 |
| ABAT | 4-aminobutyrate aminotransferase, mitochondrial | 2.28 |
| SLC25A1 | Calcium-binding mitochondrial carrier protein Aralar2 | 2.21 |
| ACADVL | Very long-chain specific acyl-CoA dehydrogenase, mitochondrial | 2.21 |
| POLRM] | DNA-directed RNA polymerase, mitochondrial | 2.18 |
| HADH | Hydroxyacyl-coenzyme A dehydrogenase, mitochondrial | 2.17 |
| COQ9 | Ubiquinone biosynthesis protein COQ9, mitochondrial | 2.12 |
| SARS2 | Serine--tRNAligase, mitochondrial | 2.12 |
| HSPA9 | Stress-70 protein, mitochondrial | 2.08 |
| CS | Citrate synthase, mitochondrial | 2.08 |
| PCCB | Propionyl-CoA carboxylase beta chain, mitochondrial | 2.05 |
| HSPD1 | 60 kDa heat shock protein, mitochondrial | 2.01 |
| DECR1 | 2,4-dienoyl-CoA reductase, mitochondrial | 2.01 |
| ACOT9 | Acyl-coenzyme A thioesterase 9, mitochondrial | 1.97 |
| GLS | Glutaminase kidney isoform, mitochondrial | 1.97 |
| ACADM | Medium-chain specific acyl-CoA dehydrogenase, mitochondrial | 1.95 |
| ATP5J | ATP synthase-coupling factor 6, mitochondrial | 1.93 |

TABLE 1-continued

Mitochondrial Proteins Upregulated During Chronic Hypoxia (96 hours) in MCF7 Cells.

| Symbol | Description | Fold-Change (Up-regulation) |
| --- | --- | --- |
| ACSM2B | Acyl-coenzyme A synthetase ACSM2B, mitochondrial | 1.86 |
| MMAB | Cob(I)yrinic acid a,c-diamide adenosyltransferase, mitochondrial | 1.86 |
| CPOX | Oxygen-dependent coproporphyrinogen-III oxidase, mitochondrial | 1.86 |
| SUCLG2 | Succinyl-CoA ligase [GDP-forming] subunit beta, mitochondrial | 1.84 |
| MRPL47 | 39S ribosomal protein L47, mitochondrial | 1.84 |
| CPT2 | Carnitine O-palmitoyltransferase 2, mitochondrial | 1.79 |
| IDH3B | Isocitrate dehydrogenase [NAD] subunit beta, mitochondrial | 1.76 |
| SLC25A2 | Calcium-binding mitochondrial carrier protein SCaMC-1 | 1.74 |
| ATPAF1 | ATP synthase mitochondrial F1 complex assembly factor 1 | 1.74 |
| NNT | NAD(P) transhydrogenase, mitochondrial | 1.73 |

Figures 8A, 8B:
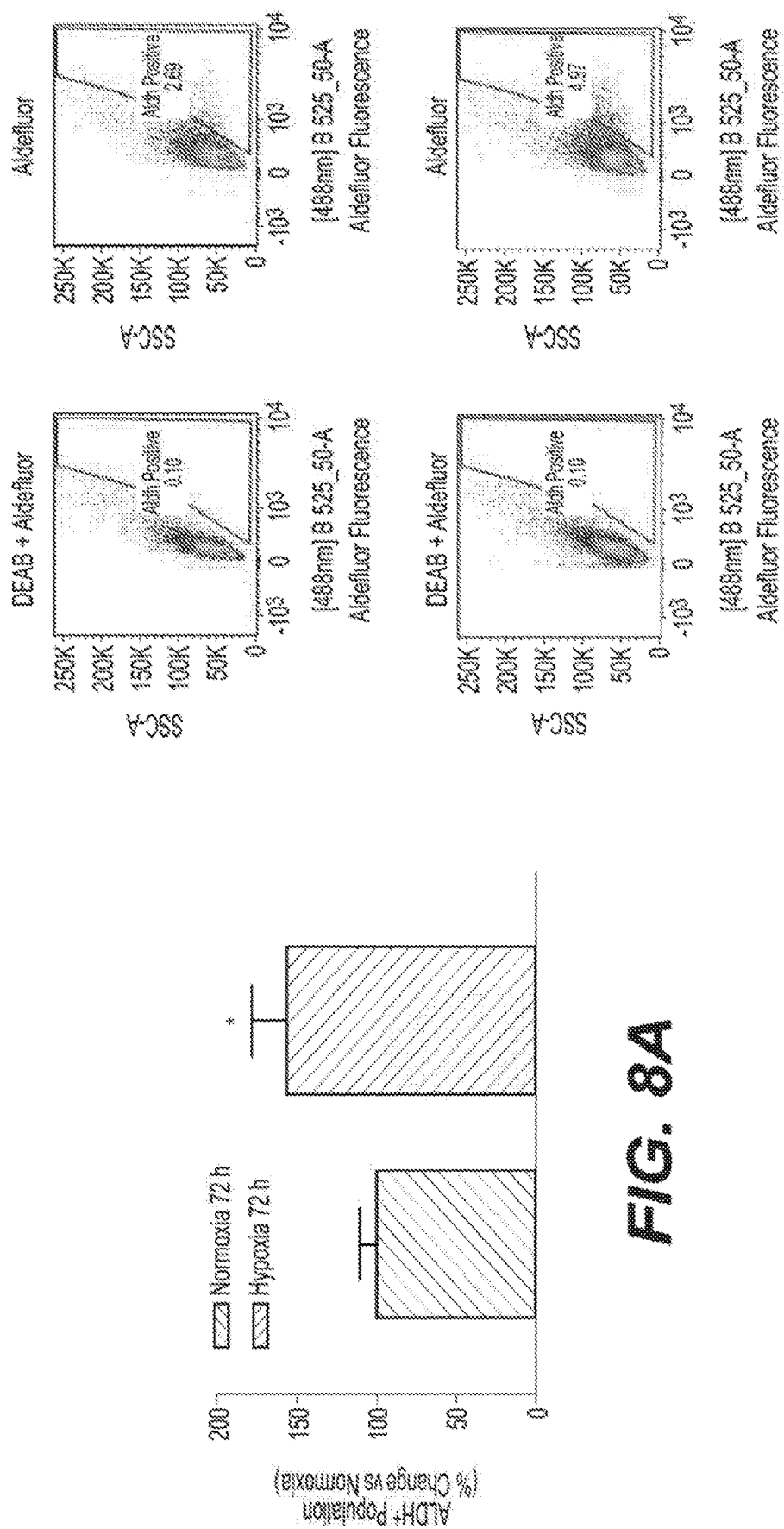
FIGS. 8A-B show the effects of hypoxia on aldehyde dehydrogenase (ALDH) activity in MCF7 cells.

The present approach further includes methods of analyzing the effects of hypoxia on CSCs by examining relative changes of CSC markers. For example, aldehyde dehydrogenase (ALDH) activity is routinely used as a marker for CSCs. It should be appreciated by those in the art that other CSC markers may be used. ALDH activity was assessed by FACS analysis in MCF7 cells cultured for 72 hours in normoxia (21% O2) or hypoxia (1% O2). The ALDEFLUOR kit (StemCell Technologies) was used to isolate the population with high ALDH enzymatic activity by FACS (Fortessa, BD Bioscence). Briefly, $1\times10^5$ MCF7 cells were incubated in 1 ml ALDEFLUOR assay buffer containing ALDH substrate (5 μl/ml) for 40 minutes at 37° C. In each experiment, a sample of cells was stained under identical conditions with 30 μM of diethylaminobenzaldehyde (DEAB), a specific ALDH inhibitor, as a negative control. The ALDEFLUOR-positive population was established in according to the manufacturer's instructions and was evaluated in $3\times10^4$ cells. Data analysis was performed using FlowJo software (Tree star Inc.). FIGS. 8A-B show that chronic hypoxia increased ALDH activity by more than 1.5-fold.

The present approach also involves methods of determining whether oxidative stress promotes chronic hypoxia-associated increases in CSC activity. The inventors quantitatively measured reactive oxygen species (ROS) production following acute and chronic hypoxia. ROS production was measured by FACS analysis using CM-H2DCFDA (C6827, Life Technologies), a cell-permeable probe that is non-fluorescent until oxidation within the cell. MCF7 cells were cultured upon normoxia (21% $O_2$) or hypoxia (1% $O_2$) for 6 hours or 96 hours. Thereafter, cells were washed with PBS and incubated at 37° C. for 20 min with 1 μM CM-H2DCFDA diluted in PBS/CM. All subsequent steps were performed in the dark. Cells were rinsed, harvested, re-suspended in PBS/CM and then analyzed by flow cytometry (Fortessa, BD Bioscience). ROS levels were estimated by using the mean fluorescent intensity of the viable cell population. The results were analyzed using FlowJo software (Tree star Inc.). FIGS. 9A-D show that chronic hypoxia induced a more than 1.5-fold increase in ROS production, whereas no increase in ROS production was observed after acute hypoxia.

Figure 9D:
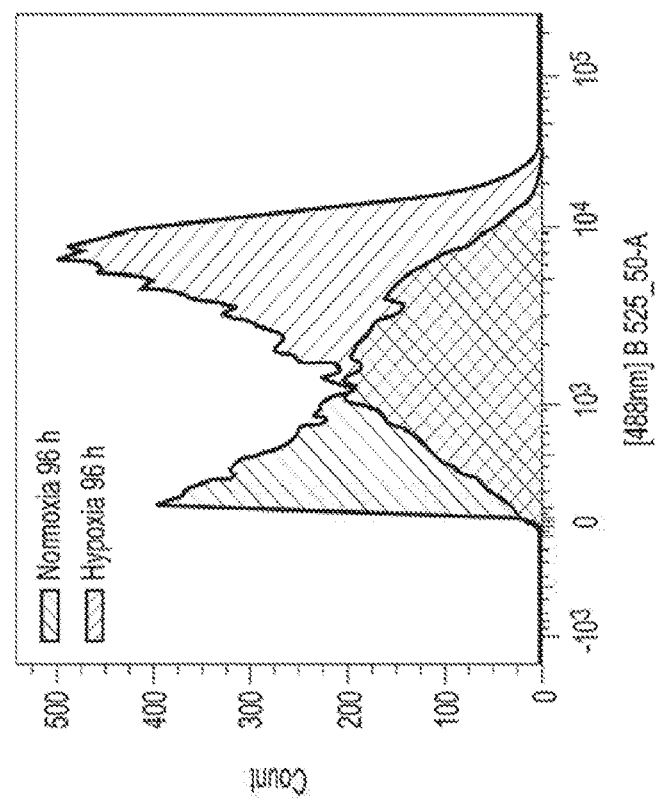
Figure 9C:
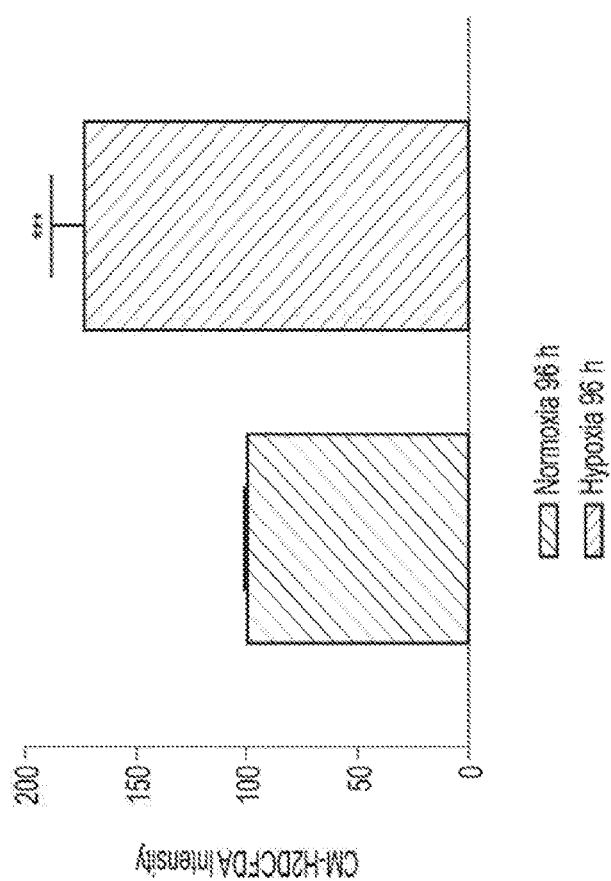
Figure 9E:
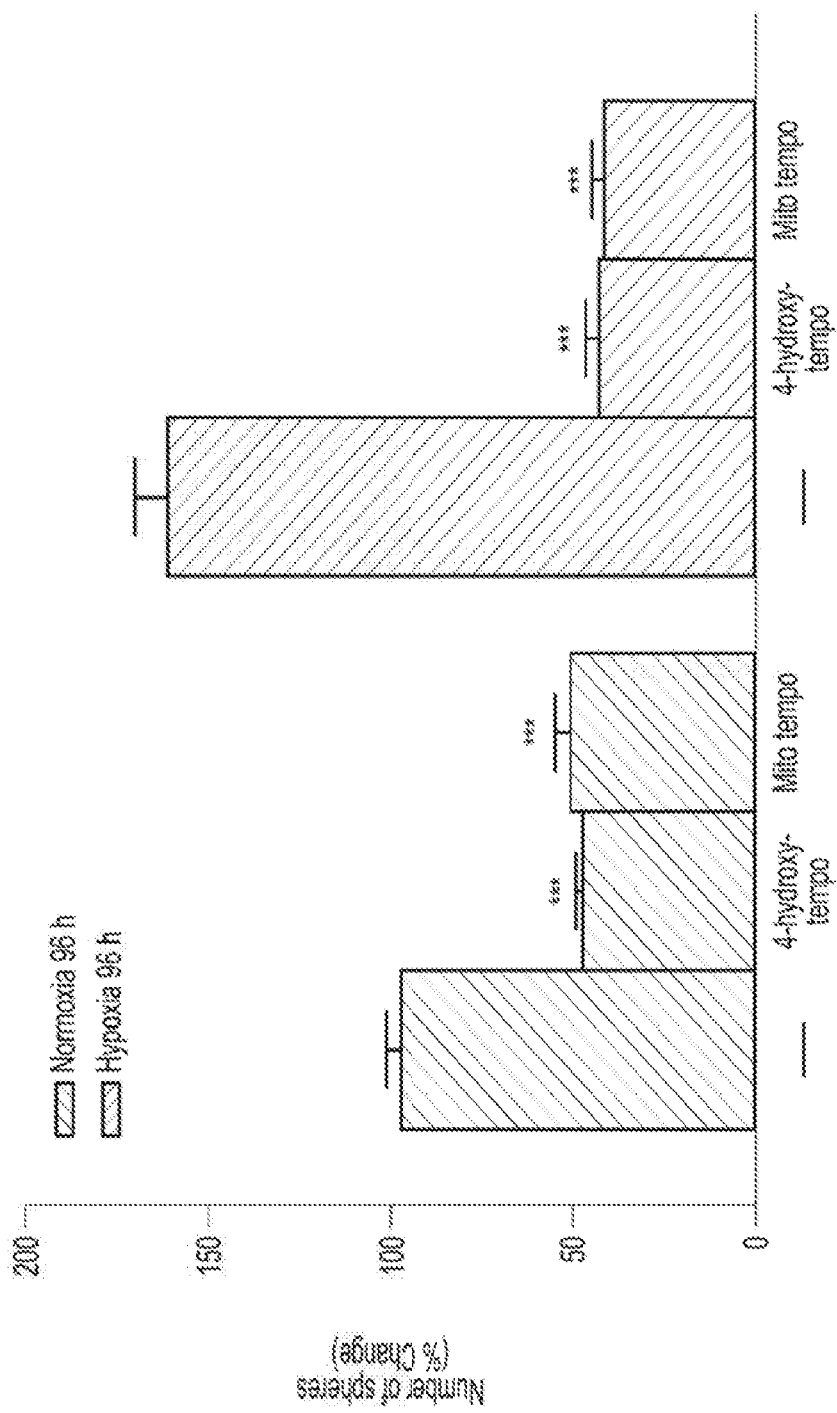
FIG. 9E shows that Mito-TEMPO inhibits mammosphere formation in MCF7 cells treated with chronic hypoxia.
Figure 10A:
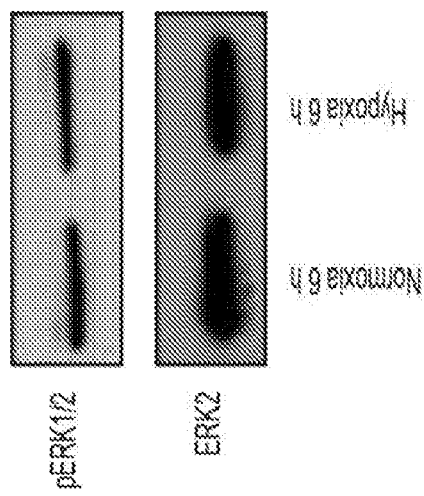
FIGS. 10A-D show that H1F1-alpha expression is upregulated during acute hypoxia but not chronic hypoxia.
Figure 10B:
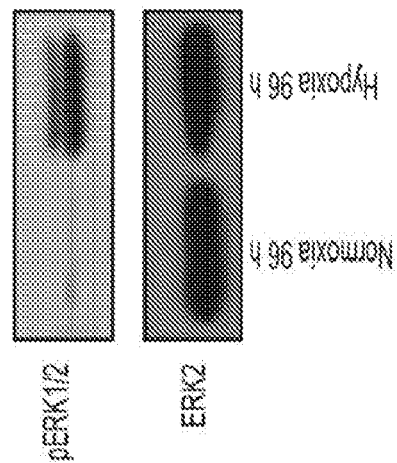
Figure 10C:
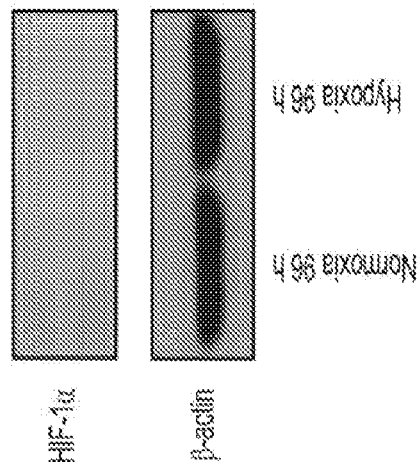
Figure 10D:
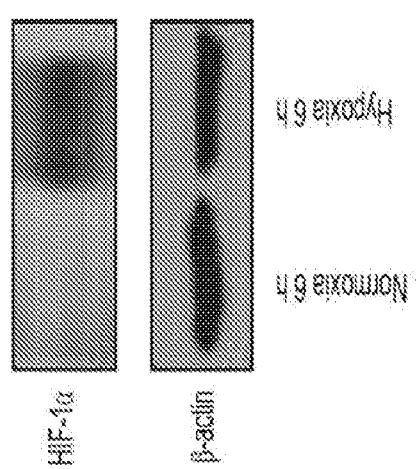
Figure 13:
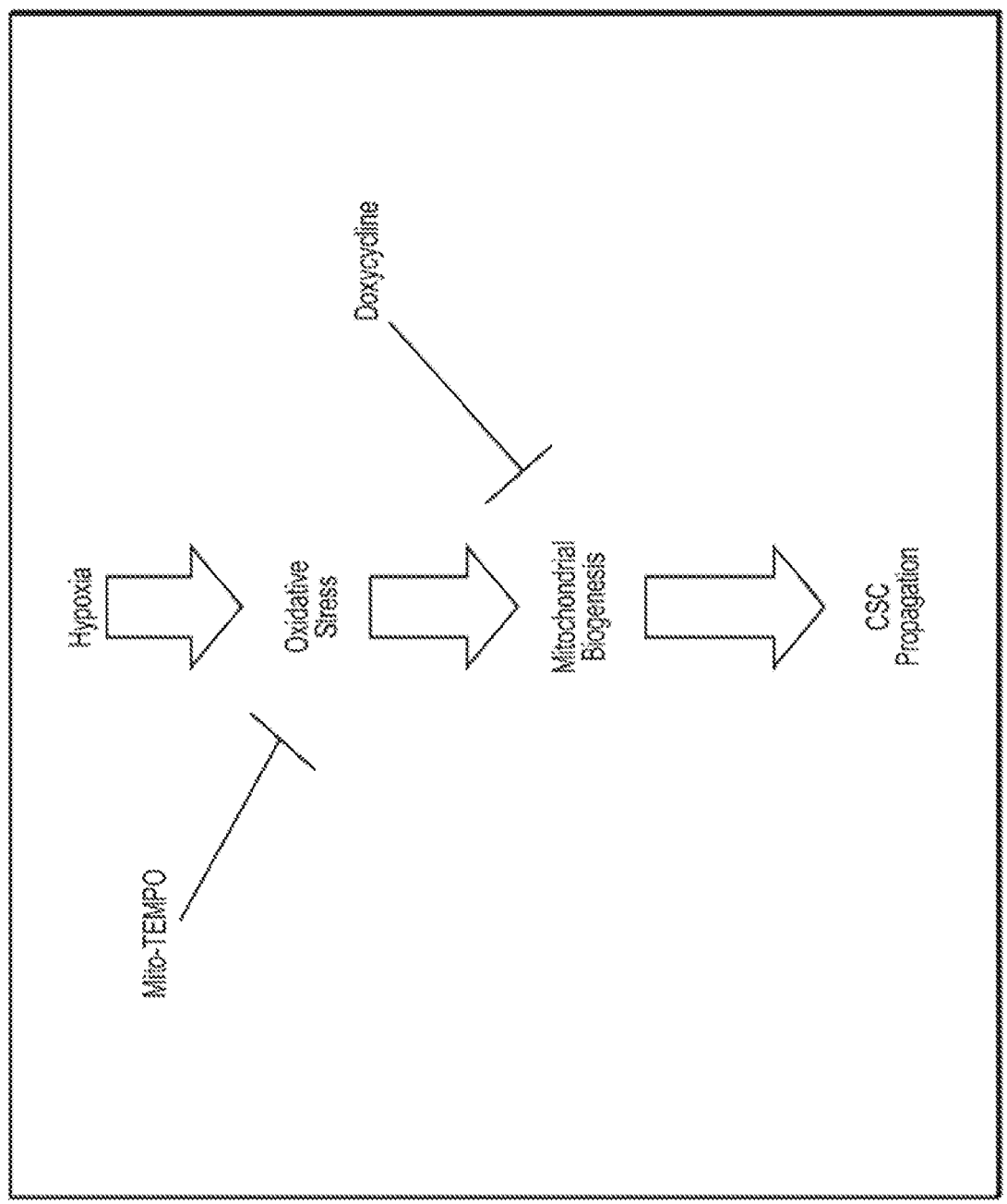
FIG. 13 outlines the means by which mitochondrial antioxidants such as Mito-Tempo and mitochondrial protein translation inhibitors such as doxycycline may be used to target hypoxic CSCs.
Figure 14:
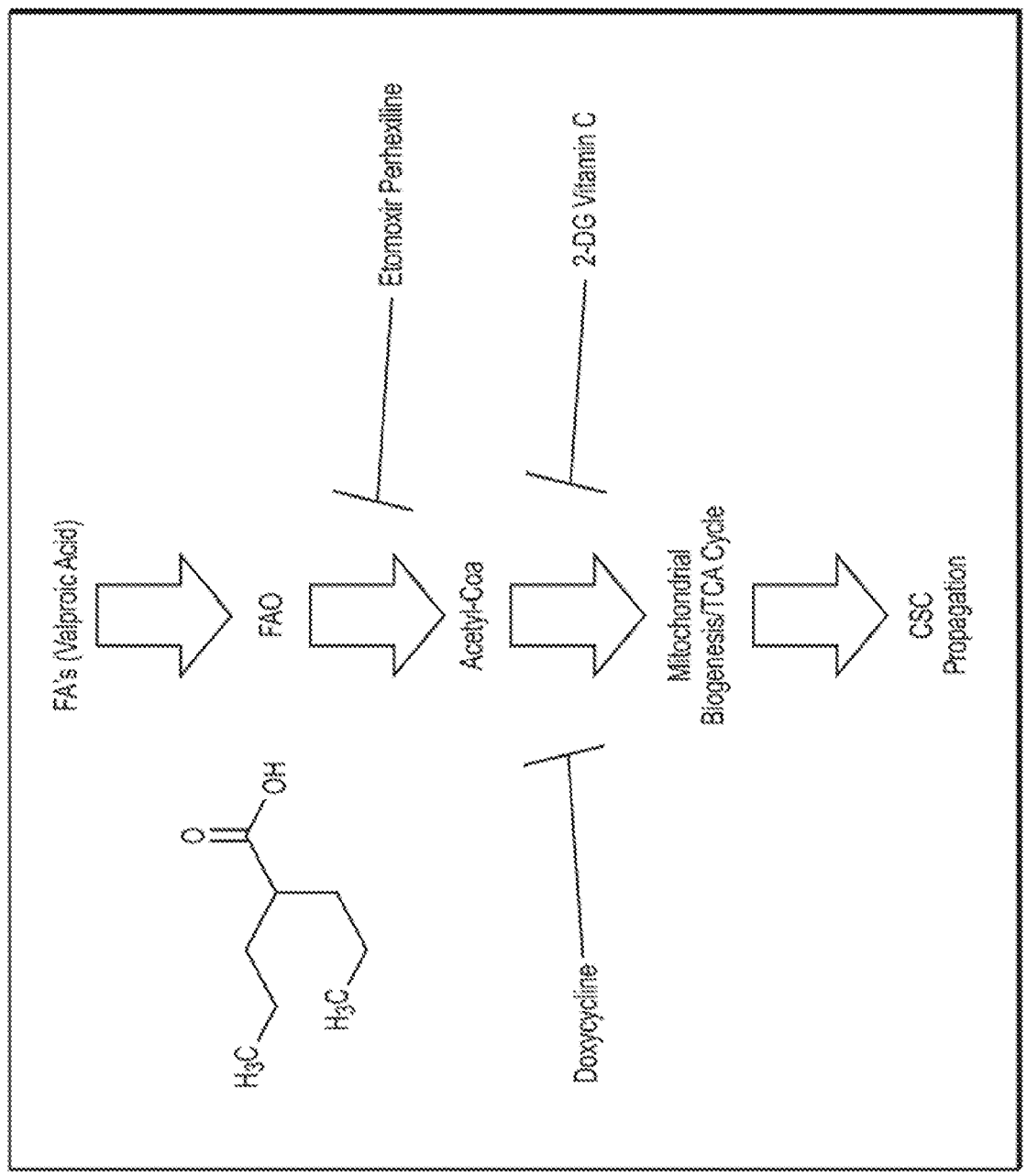
FIG. 14 summarizes how valproic acid-induced increases in CSC propagation may be blocked using fatty acid beta-oxidation (FAO) inhibitors.

To determine if oxidative stress drives the observed hypoxia-induced increase in 'sternness', the inventors determined whether simple antioxidants can inhibit mammosphere formation. For example, inventors used TEMPO-derivatives that behave as membrane-permeable sodium oxide dismutase (SOD)-mimetic agents to scavenge superoxide anions and other free radicals. FIG. 9E demonstrates that 4-hydroxy-TEMPO and Mito-TEMPO effectively inhibited mammosphere formation by more than 70% at a concentration of 100 μM. Mito-TEMPO is a mitochondrially-targeted form of TEMPO, which contains a chemical mitochondrial targeting signal. Thus, mitochondrial oxidative stress may contribute to hypoxia-induced 'sternness.' FIG. 13 summarized how doxycycline (used to target mitochondrial protein translation) and Mito-TEMPO (used as a mitochondrial antioxidant) may both be used to functionally target hypoxic CSCs.

The present approach further involves methods of determining what signaling cascades may be implicated during chronic hypoxia. For example, HIF1-alpha is a well-known transcriptional mediator of the acute effects of hypoxia, but its functional role in chronic hypoxia is less defined. The inventors examined the expression levels of HIF1-alpha and pERK-1/2 by immunoblot analysis. MCF7 cell protein lysates were electrophoresed through a reducing SDS/10% (w/v) polyacrylamide gel, electroblotted onto a nitrocellulose membrane and probed with primary antibodies against HIF1-alpha, phosphorylated ERK 1/2 (E-4), ERK2 (C-14), and β-actin (C2) (all purchased from Santa Cruz Biotechnology). Proteins were detected by horseradish peroxidase-linked secondary antibodies and revealed using the SuperSignal west pico chemiluminescent substrate (Fisher Scientific). FIG. 10 shows that HIF1-alpha was strongly upregulated during acute hypoxia but remains undetectable during chronic hypoxia. Conversely, the levels of activated phospho-ERK-1/2 were unchanged by acute hypoxia but were significantly elevated by chronic hypoxia. These two signaling molecules may contribute to metabolic signaling at different phases of the hypoxia-induced stress response. The activation of ERK-1/2 by chronic hypoxia may provide a key stimulus for enhancing anchorage-independent growth.

The present approach also includes methods of investigating the role of fatty acid oxidation (FAO) in mitochondrial biogenesis and CSC propagation. FAO is the process by which fatty acids are catabolized in mitochondria and peroxisomes to generate Acetyl-CoA, which then may enter the TCA/Krebs cycle. In the process, the energy generated for each Acetyl-CoA molecule oxidized results in 1 GTP and 11 ATP molecules. The inventors used proteomics analysis to determine what metabolic enzymes related to mitochondrial FAO are upregulated during chronic hypoxia. The inventors found that twelve mitochondrial proteins involved in FAO were induced by chronic hypoxia, including HIBADH, ACADSB, ACAD9, ACADVL, HADH, PCCB, DECR1, ACOT9, ACADM, ACSM2B, SUCLG2 and CPT2. These results are shown in Table 2.

TABLE 2

Mitochondrial Proteins Involved in Fatty Acid Oxidation Upregulated during Chronic Hypoxia.

| Symbol | Description | Fold-Change (Up-regulation) |
|---|---|---|
| HIBADH | 3-hydroxyisobutyrate dehydrogenase, mitochondrial | 8.28 |
| ACADSB | Short/branched chain specific acyl-CoA dehydrogenase, mitochondrial | 4.25 |
| ACAD9 | Acyl-CoA dehydrogenase family member 9, mitochondrial | 2.33 |
| ACADVL | Very long-chain specific acyl-CoA dehydrogenase, mitochondrial | 2.21 |
| HADH | Hydroxyacyl-coenzyme A dehydrogenase, mitochondrial | 2.17 |
| PCCB | Propionyl-CoA carboxylase beta chain, mitochondrial | 2.05 |
| DECR1 | 2,4-dienoyl-CoA reductase, mitochondrial | 2.01 |
| ACOT9 | Acyl-coenzyme A thioesterase 9, mitochondrial | 1.97 |
| ACADM | Medium-chain specific acyl-CoA dehydrogenase, mitochondrial | 1.95 |
| ACSM2B | Acyl-coenzyme A synthetase ACSM2B, mitochondrial | 1.86 |
| SUCLG2 | Succinyl-CoA ligase [GDP-forming] subunit beta, mitochondrial | 1.84 |
| CPT2 | Carnitine O-palmitoyltransferase 2, mitochondrial | 1.79 |

Figure 11A:
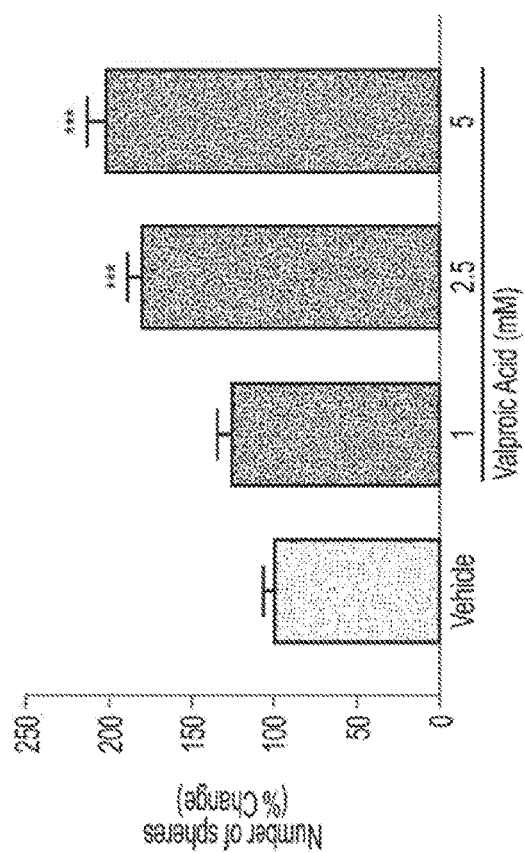
FIGS. 11A-B show that treatment with valproic acid stimulates mitochondrial biogenesis and increases mammosphere formation in MCF7 cells.
Figure 11B:
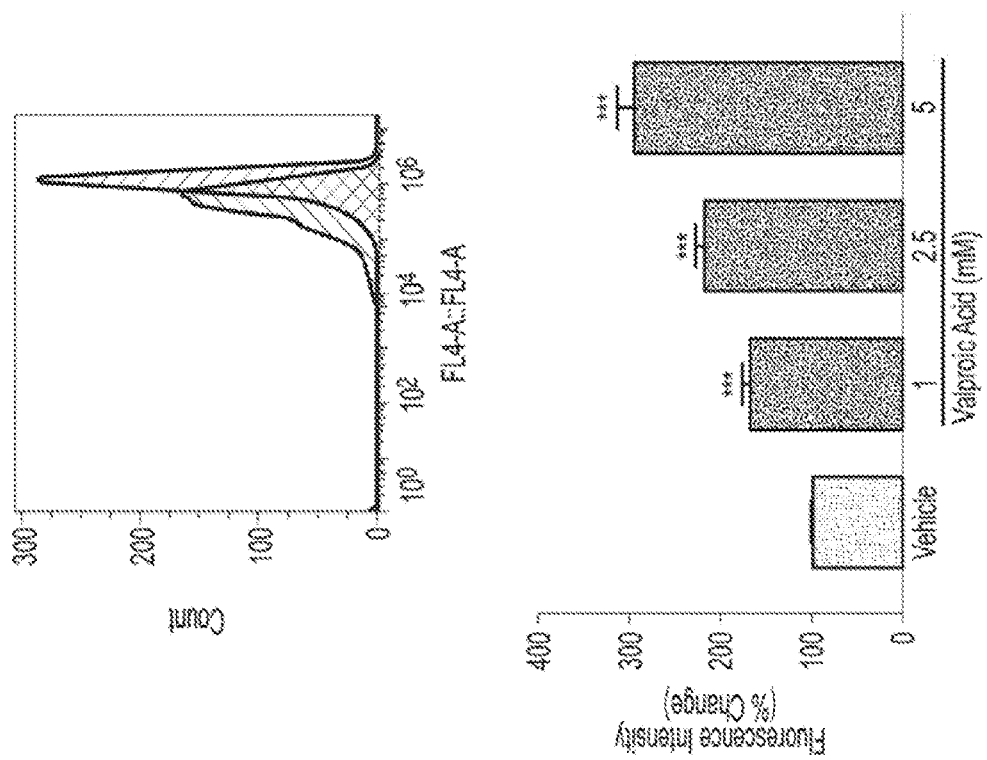
Figure 11C:
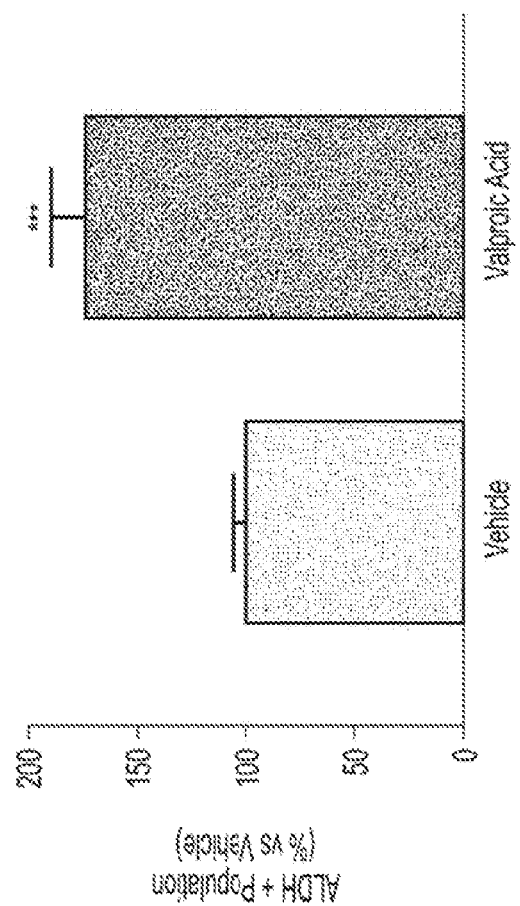
FIGS. 11C-D show that treatment with valproic acid increases ALDH activity.
Figure 11D:
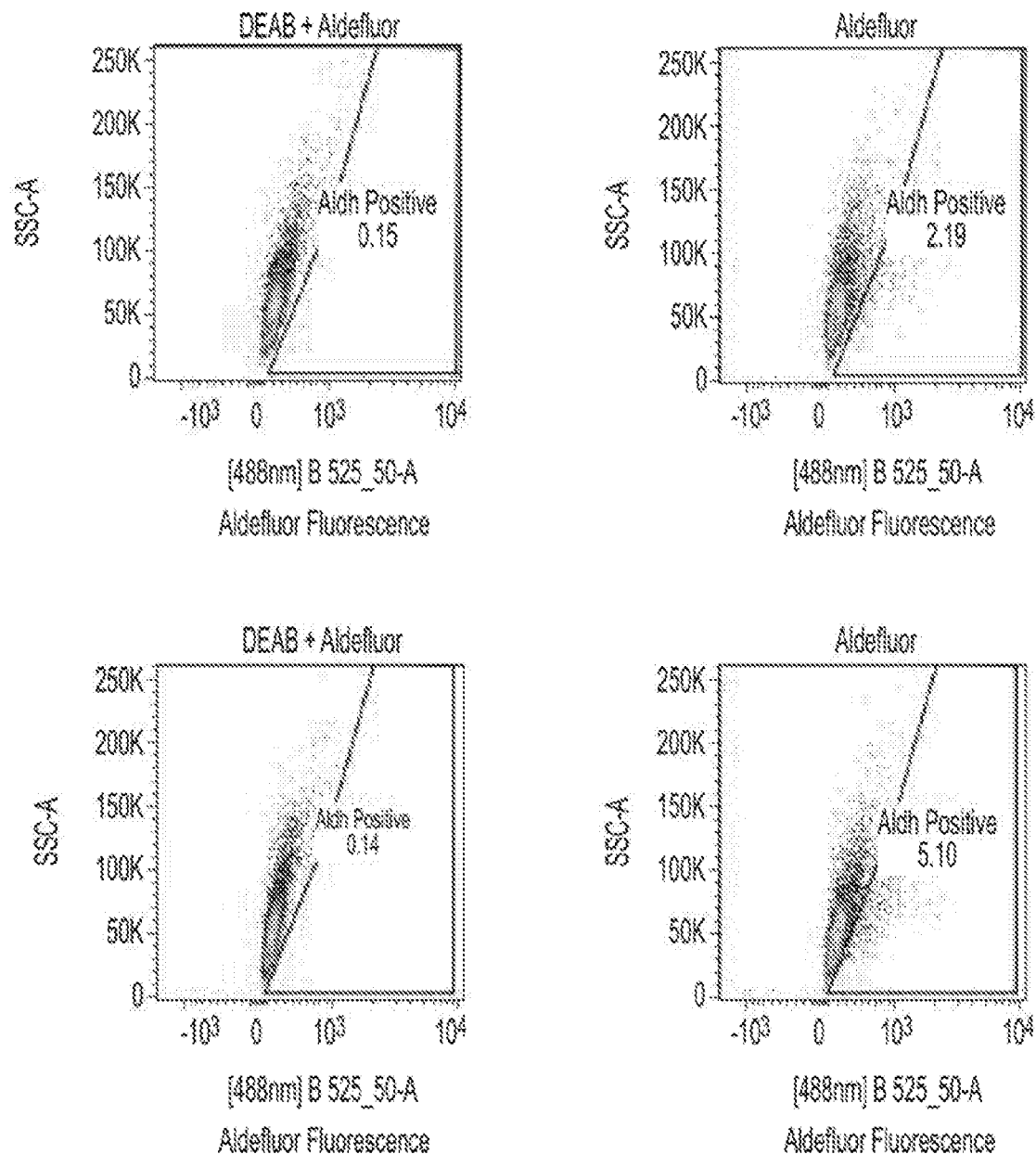

To further analyze the role of FAO in biogenesis and CSC propagation, inventors tested the effects of Valproic acid, an FDA-approved drug commonly used to treat epilepsy, on mitochondrial mass, mammosphere formation, and ALDH activity. Valproic acid is thought to behave as a fatty acid that stimulates FAO. It is chemically classified as a branched short-chain fatty acid. FIG. 11A shows that treatment with increasing concentrations of Valproic acid (0, 1, 2.5 and 5 mM) stimulates mitochondrial biogenesis, resulting in an up to 3-fold increase in mitochondrial mass. Valproic acid also increases mammosphere formation (FIG. 11B). 2.5 mM Valproic acid also increased ALDH activity by >1.5-fold, consistent with an increase in 'sternness' (FIGS. 11C-D). To validate that Valproic acid increases CSC propagation by a metabolic mechanism, the inventors tested the effects of Etomoxir and Perhexiline, two inhibitors of FAO that target the enzyme CPT (carnitine O-palmitoyltransferase). FIG. 12A-B show that Etomoxir and Perhexiline inhibit basal and Valproic acid-augmented CSC propagation. Similar results were seen with Doxycycline treatment, which inhibits mitochondrial biogenesis (FIG. 12A).

Figure 12C:
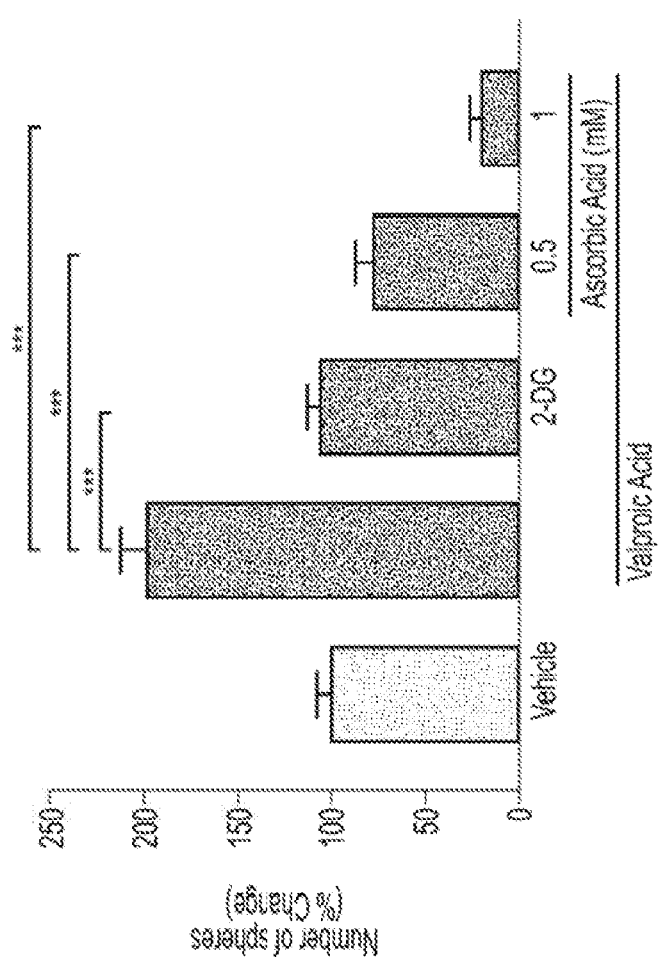

Glycolysis is required to provide additional TCA cycle intermediates for the mitochondrial processing of Acetyl-CoA. The inventors hypothesized that inhibition of glycolysis will inhibit CSC formation. Briefly, 2-deoxy-D-glucose (2-DG) or ascorbic acid were dissolved in culture medium. Treatment with glycolysis inhibitors (2-DG or Vitamin C (ascorbic acid)) was also sufficient to inhibit Valproic acid-augmented CSC propagation (FIG. 12C). The IC-50 for 2-DG was 1 mM, while the IC-50 for Vitamin C was ~0.5 mM. Vitamin C was two times as potent under Valproic acid-augmented conditions as compared to inventors' previously published results that investigated Vitamin C effects under basal conditions. Bonuccelli et al. *Oncotarget*, 8: 20667-20678 (2017). It should be appreciated that other metabolic agents/mitochondrial biogenesis inhibitors may be used in combination with anti-angiogenic agents to target CSCs. Mitochondrial biogenesis inhibitors include tetracyclines (e.g., tetracycline, doxycycline, tigecycline, and minocycline); erythromycins (e.g., eyrthromycin, azithromycin, and clarithromycin); pyrvinium pamoate; atovaquone; bedaquiline; irinotecan; sorafenib; niclosamide; berberine; stiripentol; chloroquine; etomoxir; perhexiline; mitoriboscins, such as those disclosed in U.S. Provisional Patent Application No. 62/471,688, filed Mar. 15, 2017, and Patent Cooperation Treaty (PCT) Patent Application PCT/US2018/022403, filed Mar. 14, 2018, the entireties of which are incorporated herein by reference; mitoketoscins, such as those disclosed in U.S. Provisional Patent Application No. 62/524,829, filed Jun. 26, 2017, the entirety of which is incorporated herein by reference; mitoflavoscins, such as those disclosed in U.S. Provisional Patent Application No. 62/576,287, filed Oct. 24, 2017, the entirety of which is incorporated herein by reference; TPP-compounds (e.g., 2-butene-1,4-bis-TPP), such as those disclosed in U.S. Provisional Patent Application No. 62/590,432, filed Nov. 24, 2017, the entirety of which is incorporated herein by reference; mDIVI1, such as those disclosed in U.S. Provisional Patent Application No. 62/608,065, filed Dec. 20, 2017, the entirety of which is incorporated herein by reference; CAPE (caffeic acid phenyl ester); antimitoscins, such as those disclosed in 62/508,702, filed May 19, 2017, the entirety of which is incorporated herein by reference; repurposcins such as those disclosed in U.S. Provisional Patent Application No. 62/593,372, filed Dec. 1, 2017, the entirety of which is incorporated herein by reference; other known mitochondrial inhibitors. Table 3 provides a list of metabolic agents and their respective IC-50s for inhibiting CSC propagation.

TABLE 3

Metabolic Agents and Respective IC-50s.

| DRUG | IC-50 |
|---|---|
| Doxycycline | 5 mM |
| Azithromycin | 50-100 1 mM |
| Pyrvinium pamoate | 100 nM |
| Atovaquone | 1 mM |
| Bedaquiline | 1 mM |
| Irinotecan | 500 nM |
| Sorafenib | 0.5 to 1 mM |
| Niclosamide | 100 nM |
| Berberine | 1 mM |
| 2-DG (2-deoxy-glucose) | 10-20 mM |
| Vitamin C (ascorbic acid) | 1 mM |
| Stiripentol | 10-50 mM |
| Chloroquine | <25 mM |
| Etomoxir | <200 mM |
| Perhexiline | <100 nM |
| Mitoriboscins | <5 mM; 500 nM for ATP |
| Mitoketoscins | <10 mM |
| Mitoflavoscins | 3 nM |
| TPP-compounds (e.g., 2-butene-1,4-bis-TPP) | 500 nM |
| mDIVI1 | 10 mM |
| CAPE (caffeic acid phenyl ester) | 1 mM |

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term consisting essentially of as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method of treating hypoxic cancer stem cells (CSCs) comprising:
    administering, to a cancer patient having chronic hypoxia, a therapeutically effective amount of an anti-angiogenic agent and a therapeutically effective amount of a mitochondrial biogenesis inhibitor,
    wherein the anti-angiogenic agent is selected from the group consisting of bevacizumab, itraconazole, carboxyamidotriazole, TNP-470, CM101, INF-alpha, IL-12, platelet factor-4, suramin, SU5416, thrombospondin, a VEGFR antagonist, an angiostatic steroid plus heparin, Cartilage-Derived Angiogenesis Inhibitory Factor, a matrix metalloproteinase inhibitor, angiostatin, endostatin, 2-methoxyestradiol, tecogalan, tetrathiomolybdate, thalidomide, thrombospondin, prolactin, linomide, αVβ3 inhibitors, ramucirumab, tasquinimod, ranibizumab, sorafenib, sunitinib, pazopanib, and everolimus; and
    the mitochondrial biogenesis inhibitor is selected from the group consisting of tetracycline, doxycycline, tigecycline, minocycline, eyrthromycin, azithromycin, clarithromycin, pyrvinium pamoate, atovaquone, bedaquiline, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin.

2. The method of claim 1, wherein the mitochondrial biogenesis inhibitor comprises doxycycline, and the anti-angiogenic agent comprises bevacizumab.

3. The method of claim 1, wherein the mitochondrial biogenesis inhibitor is selected from the group consisting of tetracycline, doxycycline, tigecycline, and minocycline.

4. The method of claim 1, wherein the mitochondrial biogenesis inhibitor is selected from the group consisting of eyrthromycin, azithromycin, and clarithromycin.

5. The method of claim 1, wherein the mitochondrial biogenesis inhibitor is selected from the group consisting of mitoriboscin, mitoketoscin, mitoflavoscin, TPP-compound, antimitoscin, and repurposcin.

6. The method of claim 1, wherein the cancer patient has breast cancer.

7. A method of sensitizing hypoxic cancer stem cells CSCs to a chemotherapeutic agent, the method comprising:
    administering, to a cancer patient having chronic hypoxia, a therapeutically effective amount of a mitochondrial biogenesis inhibitor with a chemotherapeutic agent; and
    wherein the mitochondrial biogenesis inhibitor comprises at least one of a tetracycline, doxycycline, tigecycline, minocycline, eyrthromycin, azithromycin, clarithromycin, pyrvinium pamoate, atovaquone, bedaquiline, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin.

8. The method of claim 7, wherein the mitochondrial biogenesis inhibitor comprises one of a tetracycline, doxycycline, tigecycline, and minocycline.

9. The method of claim 8, wherein the mitochondrial biogenesis inhibitor is doxycycline.

10. The method of claim 7, wherein the chemotherapeutic agent is paclitaxel.

11. The method of claim 7, wherein the mitochondrial biogenesis inhibitor comprises one of eyrthromycin, azithromycin, and clarithromycin.

12. The method of claim 7, wherein the mitochondrial biogenesis inhibitor comprises one of mitoriboscin, mitoketoscin, mitoflavoscin, TPP-compound, antimitoscin, and repurposcin.

13. The method of claim 7, wherein the cancer patient has breast cancer.

14. A method of sensitizing hypoxic cancer stem cells (CSCs) to radiotherapy, the method comprising:
administering, to a cancer patient having chronic hypoxia, a therapeutically effective amount of a mitochondrial biogenesis inhibitor with radiotherapy.

15. The method of claim 14, wherein the mitochondrial biogenesis inhibitor comprises a member selected from the group consisting of tetracycline, doxycycline, tigecycline, minocycline, eyrthromycin, azithromycin, clarithromycin, pyrvinium pamoate, atovaquone, bedaquiline, sorafenib, niclosamide, berberine, stiripentol, chloroquine, etomoxir, perhexiline, mitoriboscin, mitoketoscin, mitoflavoscin, TPP-compound, mDIVI1, caffeic acid phenyl ester, antimitoscin, and repurposcin.

16. The method of claim 14, wherein the mitochondrial biogenesis inhibitor is doxycycline.

\* \* \* \* \*